US007538104B2

(12) United States Patent
Baudin et al.

(10) Patent No.: US 7,538,104 B2
(45) Date of Patent: May 26, 2009

(54) PHOTOACTIVABLE NITROGEN BASES

(75) Inventors: Gisèle Baudin, Allschwil (CH); Kurt Dietliker, Allschwil (CH); Tunja Jung, Rheinfelden-Herten (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 518 days.

(21) Appl. No.: 10/491,813

(22) PCT Filed: Oct. 8, 2002

(86) PCT No.: PCT/EP02/11238

§ 371 (c)(1),
(2), (4) Date: Apr. 6, 2004

(87) PCT Pub. No.: WO03/033500

PCT Pub. Date: Apr. 24, 2003

(65) Prior Publication Data

US 2004/0242867 A1      Dec. 2, 2004

(30) Foreign Application Priority Data

Oct. 17, 2001    (CH) ..................................... 1911/01

(51) Int. Cl.
  *C07D 487/04*   (2006.01)
  *C07D 239/70*   (2006.01)
(52) U.S. Cl. .............................. 514/214.02; 514/259.1; 540/579; 544/282
(58) Field of Classification Search .............. 514/259.1, 514/214.02; 544/282; 540/579
See application file for complete search history.

(56) References Cited

U.S. PATENT DOCUMENTS

| 5,545,509 A | 8/1996 | Cameron et al. ......... 430/270.1 |
| 5,684,065 A * | 11/1997 | Hiraoka et al. .............. 523/300 |

FOREIGN PATENT DOCUMENTS

| EP | 0448154 | 9/1991 |
| EP | 0898202 | 2/1999 |
| JP | 10306141 | 11/1998 |
| WO | WO 94/28075 | 12/1994 |
| WO | WO 97/16406 | 5/1997 |
| WO | WO 97/31033 | 8/1997 |
| WO | WO 98/32756 | 7/1998 |
| WO | WO 98/38195 | 9/1998 |
| WO | WO 98/41524 | 9/1998 |
| WO | WO 00/10964 | 3/2000 |
| WO | WO 01/92362 | 12/2001 |

OTHER PUBLICATIONS

Caplus printout of Strumillo, Jozef, Synthesis of 1,3,5-Triazacycloheptane Derivatives. II. Synthesis of N-alkyl and N-aryl Derivatives of 1,2-Diaminopropane, Acta Poloniae Pharmaceutica, vol. 35, No. 1, pp. 41-45, 1978.*

Strumillo, Jozef, Synthesis of 1,3,5-Triazacycloheptane Derivatives. II. Synthesis of N-alkyl and N-aryl Derivatives of 1,2-Diaminopropane, Acta Poloniae Pharmaceutica, vol. 35, No. 1, pp. 41-45, 1978.*
J. Fréchet, Pure & Appl. Chem., vol. 64, No. 9, pp. 1239-1248, (1992).
M. Shirai et al., Prog. Polym. Sci., vol. 21, pp. 1-45, (1996).
K. Dietliker, Photobase Generators, Chapter IV, pp. 479-518, Wiley/SITA Technology, 1998.
J. Cameron et al., J. Am. Chem. Soc., (1991), vol. 113, pp. 4303-4313.
J. Cameron et al., J. Am. Chem. Soc., (1996), vol. 118, pp. 12925-12937.
K.-I. Ito et al., Journal of Polymer Science: Part A: Polymer Chemistry, vol. 32, pp. 2177-2185, (1994).
T. Nishikubo et al., Polymer Journal, vol. 25, No. 4, pp. 421-425, (1993).
T. Nishikubo et al., Journal of Polymer Science: Part A: Polymer Chemistry, vol. 31, pp. 3013-3020. (1993).
C. Kutal et al., J. Electrochem. Soc.:Solid-State Science and Technology, Sep. 1987, vol. 134, No. 9, pp. 2280-2285.
E. Urankar et al., Polym. Prepr. (1994), vol. 35, pp. 933-934.
J. Bartl et al., J. Am. Chem. Soc. (1990), vol. 112, pp. 6918-6928.
J. Hanson et al., Polym. Mater. Sci. Eng. (1995), vol. 72, pp. 201-202.
S. Hassoon et al., J. Am. Chem. Soc., (1995), vol. 117, pp. 11369-11370.
H. Tachi et al., Journal of Polymer Science: Part A: Polymer Chemistry, vol. 39, pp. 1329-1341, (2001).
R. Clemens et al., J. Coating Technol., vol. 61, No. 770, Mar. 1989, pp. 83-91.
A. Noomen, Progress in Organic Coatings, vol. 32, (1997), pp. 137-142.
R. Jones et al., Tetrahedron Letters, vol. 30, No. 39, pp. 5365-5368, (1989).

* cited by examiner

*Primary Examiner*—Brenda L Coleman
(74) *Attorney, Agent, or Firm*—Joseph C. Suhadolnik

(57) ABSTRACT

Compounds of the formula I R7"N—R6 RS—C,N—R4 H C, R'/I R, 3 R 2 (I) in which R, is an aromatic or heteroaromatic radical which is capable of absorbing light in the wave-length range from 200 nm to 650 nm and which is unsubstituted or substituted one or more times by $C_1$—$C_8$alkyl, $C_2$-$C_8$alkenyl, $C_2$-$C_8$alkynyl, $C_1$—$C_8$haloalkyl, $NO_2$, $NR_8R_9$, CN, $OR_{12}$, $SR_{12}$, $C(O)R_{13}$, $C(O)OR_{14}$, halogen or a radical of the formula II R~—N' R6 1 R5-C,N.R4 H I C—R3 I R2 (II) and which on absorption brings about a photoelimination which leads to the generation of an amidine group, R2 and R3 independently of one another are hydrogen, $C_1$—$C_8$alkyl or phenyl which is unsubstituted or is substituted one or more times by $C_1$—$C_8$alkyl, CN, $OR_{12}$, $SR_{12}$, halogen or $C_1$—$C_8$haloalkyl; R5 is $C_1$—$C_8$alkyl or $NR_8R_9$; R4, R6, R, R8, R9, $R_{10}$ and R independently of one another are hydrogen or $C_1$—$C_8$alkyl; or R4 and R6 together form a $C_2$-$C_{12}$alkylene bridge which is unsubstituted or is substituted by one or more C1-C4alkyl radicals; or R5 and R, independently of R4 and R6, together form a $C_2$-$C_{12}$alkylene bridge which is unsubstituted or is substituted by one or more C1-C4alkyl radicals; or, if R5 is a radical $NR_8R_9$, R, and R9 together form a $C_2$-$C_{12}$alkylene bridge which is unsubstituted or is substituted by one or more C1-C4alkyl radicals; and R,2, R,3 and R,4 independently of one another are hydrogen or $C_1$—$C_8$alkyl; are suitable as photoinitiators for compounds which react under base catalysis.

2 Claims, No Drawings

PHOTOACTIVABLE NITROGEN BASES

This application is a national stage entry under 35 U.S.C. 371 of PCT/EP02/11238, filed Oct. 8, 2002.

The invention relates to amines with benzylic substitution which can be converted photochemically into amidine derivatives and to a process for photochemically preparing the amidine derivatives. The invention further relates to base-polymerizable or base-crosslinkable compositions comprising these amines with benzylic substitution, to a process for conducting photochemically induced, base-catalysed reactions, and to the use of the amines with benzylic substitution as photoinitiators for base-catalysed reactions.

The photolytic generation of bases, and photopolymerization reactions of photoinduced crosslinking reactions using these bases, are described, for example, by Fréchet, J. Pure and Appl. Chem. (1992), 64, 1239, Shirai and Tsunooka, Prog. Polym. Sci. (1996), 21, 1 and Dietliker in "Photoinitiators for Free Radical, Cationic and Anionic Polymerisation", Wiley/SITA Technology 1998, chapter IV, pages 479-517. Different kinds of photolabile compounds are used here, examples being carbamates [Cameron et al., U.S. Pat. No. 5,545,509 and references cited therein; Cameron and Fréchet, J. Am. Chem. Soc. (1991) 113, 4303], α-keto carbamates [Cameron et al., J. Am. Chem. Soc. (1996) 118, 12925], O-acyl oximes [Ito et al., J. Polymer Sci.: Part A: Polymer Chem. (1994), 32, 2177], formamides [Nishikubo et al., Polym. J. (1993) 25, 421; idem, J. Polymer Sci.: Part A: Polymer Chem. (1993), 31, 3013], and co-amine complexes [C. Kutal et al., J. Electrochem. Soc. (1987), 134, 22801]. Irradiation of the compounds described produces primary or secondary amines, which can be used, for example, as crosslinkers for epoxides, isocyanates or other resin components containing functional groups which are able to react with a primary or secondary amine. In these systems, every crosslinking reaction is preceded by the photochemical liberation of an amine. The photosensitivity of such systems is therefore limited.

Formulations with a higher photosensitivity can be obtained if the photochemically liberated amine is employed as a catalyst for a base-catalysed addition, condensation or polymerization reaction. In this case the photochemically liberated amine may catalyse the formation of a large number of crosslinking steps, leading to a considerable chemical reinforcement of the photochemical reaction and thus to a higher photosensitivity, as desired.

As catalysts for, say, base-catalysed reactions, primary or secondary amines are not very suitable. Some applications of photolatent primary amines as catalysts, such as for amine-catalysed crosslinking via a Knoevenagel reaction, for example, are known (Urankar and Fréchet, Polym. Prepr. (1994), 35, 933). After the photochemical liberation of the primary amine, however, the crosslinking reaction in the presence of this weak base is very slow and incomplete at room temperature. It is therefore necessary to heat the formulation to 110° C. in order to obtain sufficient crosslinking.

A few photolabile compounds which generate tertiary amines are known. Those described include, for example, benzyl- and di- or triphenylmethane-ammonium salts [Bartl et al., J. Am. Chem Soc. (1990), 112, 6918; Hanson et al. Polym. Mater. Sci. Eng. (1995), 72, 201] and N-(benzophenonemethyl)tri-N-alkylammonium triphenylborates [Hassoon et al. J. Am. Chem. Soc. (1995), 117, 11369; WO 97/16406, Hassoon et al.)]. The irradiation of these compounds produces trialkylamines, which are better suited to use as catalysts for base-catalysed reactions than are primary or secondary amines.

N-phenacylammonium salts with N,N-dimethyldithiocarbamate counterions likewise liberate tertiary amines on irradiation [Tachi et al., J. Polym. Sci. Part A: Polym. Chem. (2001), 39, 1329]. All of these compounds are salts whose solubility in a variety of formulations is limited. From EP 898202 and WO 01/92362 it is known that from α-amino ketones it is possible to liberate tertiary amines which can be used as catalysts for base-catalysed addition or condensation reactions, such as the addition of a carboxylic acid onto an epoxide, for example. It is known that a variety of addition and condensation reactions can be catalysed to particularly good effect using amine bases whose basicity is greater than that of the customary tertiary trialkylamines. This is the case, for example, when the Michael reaction is used as a crosslinking reaction for coating materials containing, for example, acetoacetate and acrylate groups [Clemens et al., J. Coating Technol. (1989), 61, 83; Noomen, Prog. Org. Coatings (1997), 32, 137]. Especially suitable for catalysing these reactions are amines of the amidine or guanidine type. Bicyclic amidines, especially 1,8-diazabicyclo[5.4.0]undec-7-ene (DBU) and 1,5-diazabicyclo[4.3.0]non-5-ene (DBN), and also tetramethylguanidine (TMG), are out-standingly suitable catalysts for such systems and lead to much more rapid crosslinking than do tertiary trialkylamines. The addition of these strong amidine bases to formulations of this kind results in spontaneous cure at room temperature. With these compounds it is not possible to produce storage-stable one-pot systems.

There has, accordingly, been no lack of attempts to prepare strong amidine bases of this kind or other strong bases in a latent form from which the active base can be liberated by a thermal reaction or by exposure to light. By doing so it is possible to obtain one-pot systems which are stable for a fairly long time if stored in the absence of heat and/or light and which crosslink only following activation by heat or light of an appropriate wavelength. EP 448154, for example, discloses the use of amidine bases such as DBU, DBN or TMG in the form of their salts. These bases are activated thermally.

A few photolatent bases from which strong bases suitable for the catalysis of these reactions can be liberated on exposure to light, are known. For example, WO 94/28075 describes UV-deblockable bases of the amine, ammonium compound and phosphane type. As blocking agents, mention is made in particular of α-keto carboxylic acids, aromatic or N-heterocyclic formic, acetic or oxoacetic acid derivatives, with which the amine bases are converted into their non-reactive salts, and which are deblocked on irradiation. Since the salts in question are ionic salts, their solubility in the formulations is limited.

WO 97/31033 describes the photochemical liberation of bases having a $pK_a \geq 12$; as an example, N-benzyloxycarbonyltetramethylguanidine is mentioned.

Ionic salts of α-ammonium, α-iminium or α-amidinium ketones or alkenes, which liberate the corresponding tertiary amine bases on irradiation, are described, for example, in WO 98/38195 and WO 00/10964. WO 98/32756 discloses α-amino ketones from which amidine bases can be liberated on irradiation; corresponding α-amino alkenes are disclosed in WO 98/41524. The liberation of the base in this case takes place by way of an intramolecular γ-hydrogen elimination reaction, which is made possible by the special position of the double bond in the α-amino alkenes. The strong bases generated from the photolatent amines in accordance with WO 98/32756 or WO 98/41524 are suitable, for example, for catalysing reactions such as Michael addition.

There nevertheless continues to be a need for strong, photoactivable amine bases which efficiently liberate amidine bases on irradiation with UV light or visible light and which in base-curable formulations in the absence of light produce one-pot systems whose stability on storage is high.

It has now been found, surprisingly, that certain 1,3-diamine structures containing neither an α-amino ketone structure nor an α-amino alkene structure efficiently eliminate an amidine group on exposure with visible or UV light and so trigger the crosslinking reaction of a suitable formulation which can be crosslinked under base catalysis. In the absence of light the same compounds, in the same formulations which can be crosslinked by base catalysis, produce one-pot systems whose extraordinary storage stability markedly exceeds that of the systems referred to above. The 1,3-diamines are diamines substituted on one nitrogen atom by an arylalkyl radical and have the formula (I).

The invention therefore provides compounds of the formula I

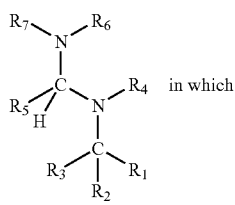

in which $R_1$ is an aromatic or heteroaromatic radical which is capable of absorbing light in the wave-length range from 200 nm to 650 nm and which is unsubstituted or substituted one or more times by $C_1$-$C_{18}$alkyl, $C_2$-$C_{18}$alkenyl, $C_2$-$C_{18}$alkynyl, $C_1$-$C_{18}$haloalkyl, $NO_2$, $NR_{10}R_{11}$, CN, $OR_{12}$, $SR_{12}$, $C(O)R_{13}$, $C(O)OR_{14}$, halogen or a radical of the formula II

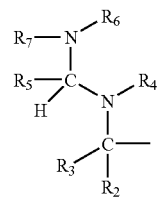

and
which on absorption brings about a photoelimination which leads to the generation of an amidine group,
$R_2$ and $R_3$ independently of one another are hydrogen, $C_1$-$C_{18}$alkyl or phenyl which is unsubstituted or is substituted one or more times by $C_1$-$C_{18}$alkyl, CN, $OR_{12}$, $SR_{12}$, halogen or $C_1$-$C_{18}$haloalkyl;
$R_5$ is $C_1$-$C_{18}$alkyl or $NR_8R_9$;
$R_4$, $R_6$, $R_7$, $R_8$, $R_9$, $R_{10}$ and $R_{11}$, independently of one another are hydrogen or $C_1$-$C_{18}$alkyl; or
$R_4$ and $R_6$ together form a $C_2$-$C_{12}$alkylene bridge which is unsubstituted or is substituted by one or more C1-C4alkyl radicals; or
$R_5$ and $R_7$, independently of $R_4$ and $R_6$, together form a $C_2$-$C_{12}$alkylene bridge which is unsubstituted or is substituted by one or more C1-C4alkyl radicals; or, if $R_5$ is a radical $NR_8R_9$, $R_7$ and $R_9$ together form a $C_2$-$C_{12}$alkylene bridge which is unsubstituted or is substituted by one or more C1-C4alkyl radicals; and
$R_{12}$, $R_{13}$ and $R_{14}$ independently of one another are hydrogen or $C_1$-$C_{19}$alkyl; with the provisos that
(i) 11-benzyl-1,11-diazabicyclo[8.4.0]tetradecane,
(ii) 10-benzyl-8-methyl-1,10-diazabicyclo[7.4.0]tridecane,
(iii) 9-benzyl-1,9-diazabicyclo[6.4.0]dodecane,
(iv) 8-benzyl-6-methyl-1,8-diazabicyclo[5.4.0]undecane, and
(v) 8-benzyl-1,8-diazabicyclo[5.4.0]undecane are excepted.

These compounds make it possible to produce what are termed one-pot systems, with base-catalysed oligomers or monomers, which possess an extraordinarily high storage stability. Only exposure to light triggers, for example, a polymerization or a crosslinking by way of addition or condensation reactions. The polymerizable or crosslinkable systems can be formulated in completely or substantially solvent-free form, since the compounds can be dissolved in the monomers or oligomers without affecting them. The active catalyst for triggering the crosslinking reaction is not produced until after exposure to light. These systems containing base-catalysable oligomers or monomers can be used for a large number of purposes, such as, for example, for paint systems, coatings, moulding compounds or photolithographic imaging systems.

Compounds not embraced by the claim are
(i) 11-benzyl-1,11-diazabicyclo[8.4.0]tetradecane:

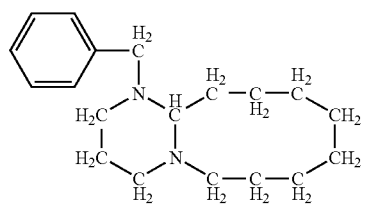

(ii) 10-benzyl-8-methyl-1,10-diazabicyclo[7.4.0]tridecane:

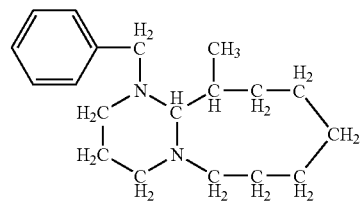

(iii) 9-benzyl-1,9-diazabicyclo[6.4.0]dodecane:

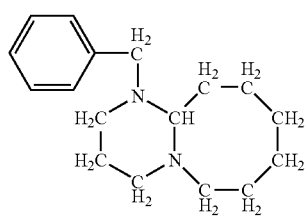

(iv) 8-benzyl-6-methyl-1,8-diazabicyclo[5.4.0]undecane:

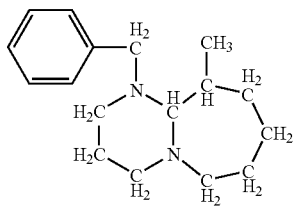

and
(v) 8-benzyl-1,8-diazabicyclo[5.4.5]undecane:

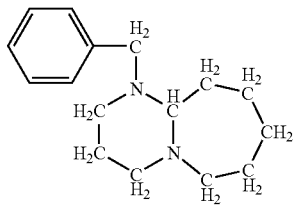

Excepted compounds are, for example, those of the formula I, as defined above, in which, if $R_1$ is phenyl, $R_2$ and $R_3$ are both hydrogen and $R_4$ and $R_6$ together form propylene, and $R_5$ and $R_7$ together are unsubstituted or methyl-substituted pentylene, hexylene, methyl-substituted heptylene or octylene.

In other words, in compounds of the formula I, if $R_1$ is phenyl, $R_2$ and $R_3$ are both hydrogen and $R_4$ and $R_6$ together form propylene, $R_5$ and $R_7$ together are not unsubstituted or methyl-substituted pentylene, are not hexylene, are not methyl-substituted heptylene and are not OC-tylene.

Aromatic or heteroaromatic radicals $R_1$ are those which obey the Hückel 4n+2 rule.

On absorbing radiation, the radical $R_1$ brings about a photoelimination reaction which leads to the generation of an amidine group. In other words, on absorption, $R_1$ brings about a cleavage of the adjacent carbon-nitrogen bond and the elimination of the hydrogen atom located on the carbon atom between the two nitrogen atoms in the formula I, so forming an amidine double bond.

Through the choice of the aromatic or heteroaromatic radical $R_1$ it is possible to vary the maximum of the absorption within a wide range and so to shift the photosensitivity of the compounds from the UV region into the daylight region.

Alkyl in the various radicals having up to 18 carbon atoms is a branched or unbranched radical, such as $C_1$-$C_{18}$-, $C_1$-$C_{12}$-, $C_1$-$C_{10}$-, $C_1$-$C_8$-, $C_1$-$C_6$-, $C_1$-$C_4$-, $C_2$-$C_{18}$-, $C_2$-$C_{12}$- or $C_2$-$C_4$alkyl, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl. Preference is given to alkyl having from 1 to 12 carbon atoms, in particular from 1 to 6 carbon atoms.

Alkenyl having from 2 to 18 carbon atoms is a branched or unbranched radical, such as $C_2$-$C_{18}$-, $C_2$-$C_{12}$-, $C_2$-$C_8$-, $C_3$-$C_{18}$-, $C_3$-$C_8$alkenyl, for example ethenyl, propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. Preference is given to alkenyl having from 2 to 12 carbon atoms, in particular from 2 to 6 carbon atoms.

Alkynyl having from 2 to 18 carbon atoms is a branched or unbranched radical such as ethynyl (—C≡CH), propynyl

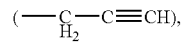

2-butynyl, 3-butynyl, n-2-octynyl or
n-2-octadecynyl, for example. Preference is given to alkynyl having from 2 to 12 carbon atoms, in particular from 2 to 6 carbon atoms.

Examples of $C_2$-$C_{12}$alkylene bridges are ethylene, propylene, butylene, pentylene, hexylene, heptylene, octylene, nonylene, decylene, undecylene or dodecylene. These bridges are, for example, unsubstituted or substituted by one or more C1-C4alkyl radicals. $C_1$-$C_4$alkyl is as described above up to the corresponding number of carbon atoms.

Where a definition refers to one or more substituents, there are for example from 1 to 4, from 1 to 3, 1 or two, preferably one, substituent(s) present.

$C_1$-$C_{18}$Haloalkyl is a $C_1$-$C_{18}$alkyl as described above which is substituted by one or more halogens. The number of halogen atoms may correspond to the hydrogen atoms normally present in the alkyl; in other words, the alkyl radical in question can be perhalogenated. Examples are the positional isomers of mono- to undecafluoropentyl, mono- to nonafluorobutyl, mono- to heptafluoropropyl, mono- to pentafluoroethyl, and mono-, di- and trifluoromethyl, and also the corresponding chlorine, bromine and iodine compounds. The perfluorinated alkyl radicals are preferred. Examples thereof are perfluoropentyl, perfluorobutyl, perfluoropropyl, perfluoroethyl and, in particular, trifluoromethyl.

Halogen is Cl, F, Br or I, especially Cl, F or Br, preferably Cl.

Examples of the $NR_8R_9$ or $NR_{10}R_{11}$ amino groups are a respective monoalkylamino or dialkylamino groups such as methylamino, ethylamino, propylamino, butylamino, pentylamino, hexylamino, octadecylamino, dimethylamino, diethylamino, dipropylamino, diisopropylamino, di-n-butylamino, di-isobutylamino, dipentylamino, dihexylamino or dioctadecylamino. Further dialkylamino groups are those in which the two radicals independently of one another are branched or unbranched, such as methylethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, isopropyl-n-butylamino or isopropyliso-butylamino.

The group $OR_{12}$ having up to 18 carbon atoms is either OH or a branched or unbranched radical such as methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Preference is given to alkoxy having from 1 to 12 carbon atoms, in particular from 1 to 8 carbon atoms, for example from 1 to 6 carbon atoms.

Examples of the group $SR_{12}$ are SH, thiomethyl, thioethyl, thiopropyl, thiobutyl, thiopentyl, thiohexyl, thioheptyl, thiooctyl or thiooctadecyl, the alkyl radicals being linear or branched.

Examples of $R_1$ as an aromatic radical or as a heteroaromatic radical are phenyl, naphthyl, both 1-naphthyl and 2-naphthyl, phenanthryl, anthryl, preferably 1-anthryl but also 2-anthryl and 9-anthryl, biphenylyl, pyrenyl, 5,6,7,8- tetrahydro-2-naphthyl, 5,6,7,8-tetrahydro-1-naphthyl, thienyl, benzo[b]thienyl, naphtho[2,3-b]thienyl, thianthrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, fluorenyl, phenoxazinyl, methoxyphenyl, 2,4-dimethoxyphenyl, 2,4,6-trimethoxyphenyl, 3,4,5-trimethoxyphenyl, bromophenyl, 2-chlorophenyl, 2,6-dichlorophenyl, 3-cyanophenyl, 4-cyanophenyl, 3-methoxyphenyl, 4-methoxyphenyl, 4-hydroxyphenyl, 2-hydroxyphenyl, toluyl, xylyl, mesityl, nitrophenyl, dimethylaminophenyl, diethylaminophenyl, aminophenyl, diaminophenyl, thiomethylphenyl, 1-phenylamino-4-naphthyl, 1-methylnaphthyl, 2-methylnaphthyl, 1-methoxy-2-naphthyl, 2-methoxy-1-naphthyl, 1-dimethylamino-2-naphthyl, 1,2-dimethyl-4-naphthyl, 1,2-dimethyl-6-naphthyl, 1,2-dimethyl-7-naphthyl, 1,3-dimethyl-6-naphthyl, 1,4-dimethyl-6-naphthyl, 1,5-dimethyl-2-naphthyl, 1,6-dimethyl-2-naphthyl, 1-hydroxy-2-naphthyl, 2-hydroxy-1-naphthyl, 1,4-dihydroxy-2-naphthyl, 7-phenanthryl, anthraquinone-2-yl (=9,10-dioxo-9,10-dihydroanthracen-2-yl), 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxyathiinyl, 2,7-phenoxathiinyl, 2-pyrrolyl, 3-pyrrolyl, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2quinolizinyl, 3-isoquinolyl, 6-isoquinolyl, 7-isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 2-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl or 10-methyl-2-phenoxazinyl.

The term "and/or" is intended to express the fact that not just one of the alternatives defined (substituents) may be present but that it is likewise possible for there to be two or more different alternatives (substituents) from among those defined, together, i.e. mixtures of different alternatives (substituents).

The term "at least" is intended to define one or more than one, e.g. one or two or three, preferably one or two.

In the description and the claims, the word "comprising" is to be understood to mean that a defined subject or a defined group of subjects is included but without ruling out any other substances not explicitly mentioned, unless expressly described otherwise.

Preferred compounds of the formula I are those wherein $R_1$ is phenyl, naphthyl, phenanthryl, anthryl, pyrenyl, 5,6,7,8-tetrahydro-2-naphthyl, 5,6,7,8-tetrahydro-1-naphthyl, thienyl, benzo[b]thienyl, naphtho[2,3-b]thienyl, thianthrenyl, anthraquinonyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, stilbenyl, fluorenyl or phenoxazinyl, these radicals being unsubstituted or substituted one or more times by $C_1$-$C_{18}$alkyl, $C_2$-$C_{18}$alkenyl, $C_2$-$C_{18}$alkynyl, $C_1$-$C_{18}$haloalkyl, $NO_2$, $NR_{10}R_{11}$, CN, $OR_{12}$, $SR_{12}$, $C(O)R_{13}$, $C(O)OR_{14}$, halogen or a radical of the formula II, or $R_1$ is a radical of the

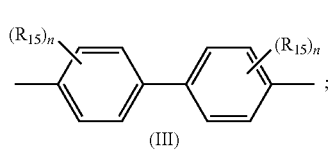

formula III $R_{12}$, $R_{13}$ and $R_{14}$ independently of one another are hydrogen or $C_1$-$C_{18}$alkyl;

$R_{15}$ is $C_1$-$C_{18}$alkyl, $C_2$-$C_2$-$C_{18}$alkenyl, OH, CN, $OR_{10}$, $SR_{10}$, halogen or a radical of formula II; and n is 0, 1, 2 or 3.

With particular preference $R_1$ is phenyl, naphthyl, anthryl, anthraquinon-2-yl, biphenylyl, pyrenyl, thioxanthyl, thianthrenyl or phenothiazinyl, these radicals being unsubstituted or being substituted one or more times by $C_1$-$C_{18}$alkyl, $C_1$-$C_{18}$haloalkyl, $NR_{10}R_{11}$, CN, $NO_2$, $SR_{12}$, $OR_{12}$ or a radical of formula III or $R_1$ is a radical of the formula III above.

Further particularly preferred compounds are those wherein $R_1$ is phenyl, anthryl, naphthyl, anthraquinon-2-yl or biphenylyl, the radicals phenyl, anthryl, naphthyl, anthraquinon-2-yl and biphenylyl being unsubstituted or being substituted one or more times by CN, $NR_{10}R_{11}$, $NO_2$, $CF_3$, $SR_{12}$, $OR_{12}$ or a radical of the formula II or $R_1$ is a radical of the formula III as defined above.

With very particular preference $R_1$ is phenyl, 4-methylphenyl, biphenylyl, 2,4,6-trimethylphenyl, 4-cyanophenyl, 3-cyanophenyl, 2-chlorophenyl, 2,6-dichlorophenyl, 3-methoxyphenyl, 4-methoxyphenyl, 4-ethenylphenyl, 4-methylthiophenyl, 4-trifluoromethylphenyl, 2-nitrophenyl, 2,4,6-trimethoxyphenyl, 2,4-dimethoxyphenyl, naphthyl, anthryl or anthraquinon-2-yl or $R_1$ is one of the aforementioned radicals which is additionally substituted by a radical of the formula II.

Preferably, $R_2$ and $R_3$ independently of one another are hydrogen or $C_1$-$C_6$alkyl.

Likewise preferably, $R_4$ and $R_6$ together are a $C_2$-$C_6$alkylene bridge which is unsubstituted or is substituted by one or more $C_1$-$C_4$alkyl radicals.

Preferably, $R_5$ and $R_7$ in the compounds of the formula I are together a $C_2$-$C_6$alkylene bridge which is unsubstituted or is substituted by one or more $C_1$-$C_4$alkyl radicals or, if $R_5$ is NR$_8$R$_9$, R$_9$ and R$_7$ together form a C$_2$-C$_6$alkylene bridge which is unsubstituted or substituted by one or more C$_1$-C$_4$alkyl radicals.

One particularly preferred group of compounds of the formula I are those wherein R$_1$ is phenyl, naphthyl, anthryl, anthraquinonyl, thianthrenyl, fluorenyl or thioxanthyl, these radicals being unsubstituted or being substituted one or more times by C$_1$-C$_4$alkyl, C$_2$-C$_4$alkenyl, CN, NR$_{10}$R$_{11}$, NO$_2$, CF$_3$, SR$_{12}$, OR$_{12}$, halogen or a radical of the formula II, or R$_1$ is a radical of the formula III;

n is 0 or 1;

R$_{10}$, R$_{11}$ and R$_{12}$ are hydrogen or C$_1$-C$_6$alkyl;

R$_2$ and R$_3$ are hydrogen or C$_1$-C$_6$alkyl;

R$_4$ and R$_6$ together form a C$_2$-C$_6$alkylene bridge which is unsubstituted or is substituted by one or more C$_1$-C$_4$alkyl radicals;

R$_5$ and R$_7$ together form a C$_2$-C$_6$alkylene bridge which is unsubstituted or is substituted by one or more C$_1$-C$_4$alkyl radicals; and R$_{15}$ is C$_1$-C$_4$alkyl, halogen or a radical of the formula II.

Particular preference is given to compounds of the formula I wherein

R$_1$ is phenyl, naphthyl, anthryl or anthraquinonyl, these radicals being unsubstituted or being substituted one or more times by halogen, C$_1$-C$_4$alkyl, C$_2$-C$_4$alkenyl, NO$_2$, CN, OR$_{12}$ or a radical of the formula II, R$_{12}$ is hydrogen or C$_1$-C$_4$alkyl;

R$_2$ and R$_3$ are hydrogen or C$_1$-C$_6$alkyl;

R$_4$ and R$_6$ together form a C$_2$-C$_6$alkylene bridge which is unsubstituted or is substituted by one or more C$_1$-C$_4$alkyl radicals; and R$_5$ and R$_7$ together form a C$_2$-C$_6$alkylene bridge which is unsubstituted or is substituted by one or more C$_1$-C$_4$alkyl radicals.

The compounds of the invention can be prepared by various processes known to the person skilled in the art.

By way of example, compounds of the formula (I) can be prepared by reacting compounds of the formula (VI)

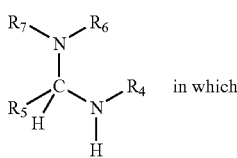

(VI) in which

R$_4$, R$_5$, R$_6$ and R$_7$ are as defined above, including the preferred definitions, with a compound of the formula (VII)

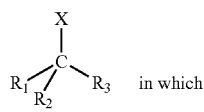

(VII) in which

R$_1$, R$_2$ and R$_3$ are as defined above, including the preferred definitions, X is a halogen atom, OCOR$_{16}$ or OSO$_2$R$_{16}$, and R$_{16}$ is C$_1$-C$_8$alkyl, perfluoroalkyl or aryl which is substituted by one or more C1-C4 alkyl radicals or by fluorine.

Halogen is preferably bromine or chlorine.

The reaction of compounds of the formula (VI) with compounds of the formula (VII) can be carried out in a manner known per se. It is advantageous to use a solvent or mixture of solvents, examples being hydrocarbons such as benzene, toluene, xylene, etc., halogenated hydrocarbons, such as methylene chloride, chloroform, carbon tetrachloride, chlorobenzene, etc., alkanols such as methanol, ethanol, ethylene glycol monomethyl ether, etc., and ethers such as diethyl ether, dibutyl ether, ethylene glycol dimethyl ether, ketones such as acetone or 2-butanone or dimethyl sulfoxide. It is also possible to use mixtures of such solvents. It is appropriate to add a base to the reaction mixture. Suitable bases are tertiary amines such as, for example, triethylamine, triethanolamine, 2,2,6,6-tetramethylpiperidine, etc. Also suitable are inorganic bases such as sodium hydroxide, potassium hydroxide, sodium carbonate, potassium carbonate, calcium oxide, sodium hydrogen carbonate, etc.

The reaction can be carried out, for example, within a temperature range from −10° C. to +100° C. Preference is given to ranges from +10° C. to +70° C.

Additionally, compounds of the formula (I) can also be prepared, for example, by reacting a compound of the formula (V)

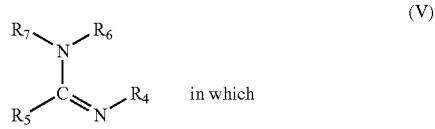

(V) in which

R$_4$, R$_5$, R$_6$ and R$_7$ are as defined above, including the preferred definitions, with a compound of the formula (VII)

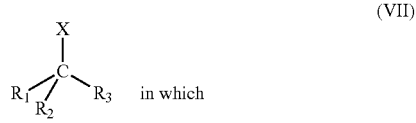

(VII) in which

R$_1$, R$_2$ and R$_3$ are as defined above, including the preferred definitions;

X is a halogen atom, OCOR$_{16}$ or OSO$_2$R$_{16}$; and

R$_{16}$ is C$_1$-C$_8$alkyl, perfluoroalkyl or aryl which is substituted by one or more C1-C4 alkyl radicals or by fluorine;

and subjecting the reaction product to subsequent reduction.

Halogen is preferably bromine or chlorine.

The reaction of compounds of the formula (V) with compounds of the formula (VII) can be carried out in a manner known per se. It is advantageous to use a solvent or mixture of solvents, examples being hydrocarbons such as benzene, toluene, xylene, etc., halogenated hydrocarbons, such as methylene chloride, chloroform, carbon tetrachloride, chlorobenzene, etc., alkanols such as methanol, ethanol, ethylene glycol monomethyl ether, etc., and ethers such as diethyl ether, dibutyl ether, tert-butyl methyl ether, ethylene glycol dimethyl ether, tetrahydrofuran, ketones such as acetone or 2-butanone or dimethyl sulfoxide. It is also possible to use mixtures of such solvents.

The reaction can be carried out, for example, within a temperature range from −10° C. to +100° C. Preference is given to ranges from 0° C. to +70° C.

The reaction described above produces a quaternary ammonium salt. This salt can be isolated or else converted directly by treatment with an appropriate reducing agent into the compounds of the formula (I) according to the invention. Reduction to the compounds of the formula (I) according to the invention can be carried out in accordance with a variety of processes which are known to the person skilled in the art. Suitable reducing agents, for example, are metal hydrides such as lithium aluminium hydride, sodium borohydride, sodium cyanoborohydride or dibutylaluminium hydride. Likewise suitable are reducing agents such as polymethylhydrosiloxanes in combination with an appropriate activator (Lawrence et al., J. Chem. Soc. Perkin Trans. I.(1999), 3381). Additionally, the catalytic reduction can be carried out with hydrogen, using the metal catalysts which are customary in the art and are known to the person skilled in the art.

It is appropriate to use a solvent or mixture of solvents, examples being hydrocarbons such as benzene, toluene, xylene, etc., ethers such as diethyl ether, dibutyl ether, tert-butyl methyl ether, ethylene glycol dimethyl ether or tetrahydrofuran. Under specific conditions, depending on the base used, alkanols such as methanol, ethanol, etc. are also suitable. The reaction can be carried out, for example, within a temperature range from −30° C. to +100° C. Preference is given to ranges from −10° C. to +30° C.

Compounds of the formula (I), in which $R_4$ and $R_6$ together are a $C_2$-$C_{12}$alkylene bridge and $R_5$ and $R_7$ together are a $C_3$-$C_{12}$alkylene bridge may also be prepared, for example, by way of a rhodium-catalysed hydroformylation reaction, starting from appropriate N-alkenyl-α,ω-diamines. This process is described, for example, by Bergmann et al. in Aust. J. Chem. (1999), 52, 1131. The N-alkenyl-α,ω-diamine is reacted with carbon monoxide and hydrogen in an inert solvent, such as benzene, for example, under pressure and with rhodium catalysis. Examples of suitable catalysts are rhodium complexes such as may be prepared in situ, for example, from rhodium acetate and a phosphine such as triphenylphosphine or 6,6'-{[3,3'-bis(1,1-dimethylethyl)-5,5'-dimethoxy-1,1'-biphenyl]-2,2'-diyl}bis(oxy)-bis(dibenzo[d,f][1,3,2]dioxaphosphepine (BIPHEPHOS).

Compounds of the formula (I) can also be prepared by further synthesis processes which are known to the person skilled in the art.

In the preparation of the photolatent bases of the invention, isomer mixtures may be formed.

These mixtures can be separated, for example, by customary methods which are known to the person skilled in the art. However, it is also possible to use each of the isomer mixtures formed as photolatent bases directly.

The invention further provides a process for preparing a compound of the formula (V)

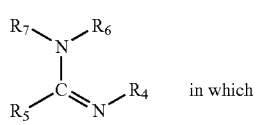

(V) in which $R_5$ is $C_1$-$C_{18}$alkyl or $NR_8R_9$;
$R_4$, Re, $R_7$, $R_5$ and $R_9$ independently of one another are hydrogen or $C_1$-$C_{18}$alkyl; or
$R_4$ and $R_8$ together form a $C_2$-$C_{12}$alkylene bridge which is unsubstituted or is substituted by one or more $C_1$-$C_4$alkyl radicals; or
$R_5$ and $R_7$, independently of $R_4$ and $R_5$, together form a $C_2$-$C_{12}$alkylene bridge which is unsubstituted or is substituted by one or more $C_1$-$C_4$alkyl radicals; or,
if $R_5$ is a radical $NR_8R_9$, $R_7$ and $R_9$ together form a $C_2$-$C_{12}$alkylene bridge which is unsubstituted or is substituted by one or more $C_1$-$C_4$alkyl radicals;

which comprises subjecting a compound of the formula (I)

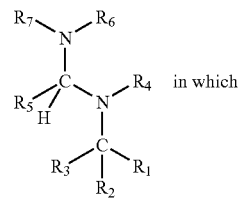

(I) in which $R_1$ is an aromatic or heteroaromatic radical which is capable of absorbing light in the wavelength range from 200 nm to 650 nm and is unsubstituted or is substituted one or more times by $C_1$-$C_{18}$alkyl, $C_2$-$C_{18}$alkenyl, $C_2$-$C_{18}$alkynyl, $C_1$-$C_{18}$haloalkyl, $NO_2$, $NR_{10}R_{11}$, CN, $OR_{12}$, $SR_{12}$, $C(O)R_{13}$, $C(O)OR_{14}$, halogen or a radical of the formula II

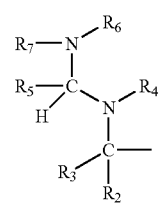

(II)

and which on absorption brings about a photoelimination which leads to the generation of an amidine group;
$R_2$ and $R_3$ independently of one another are hydrogen, $C_1$-$C_{18}$alkyl or are phenyl which is unsubstituted or is substituted one or more times by $C_1$-$C_{18}$alkyl, CN, $OR_{12}$, $SR_{12}$, halogen or $C_1$-$C_{18}$haloalkyl;
$R_5$, $R_4$, $R_6$, $R_7$, $R_8$, $R_9$, $R_{10}$ and $R_{11}$ are as defined above; and
$R_{12}$, $R_{13}$ and $R_{14}$ are independently of one another hydrogen or $C_1$-$C_{18}$alkyl;

to irradiation with light having a wavelength of from 200 nm to 650 nm. Where appropriate, a suitable sensitizer, such as a substituted or unsubstituted benzophenone or a substituted or unsubstituted thioxanthone, for example, may be added. Suitable sensitizer compounds (C) are described later on below.

The reaction is conducted, for example, in a solvent or solvent mixture or in a mixture of oligomers and/or polymers and, where appropriate, a solvent. The concentration of the compounds of the formula (I) is advantageously set such that absorption of the light in the reaction vessel is virtually complete.

The reaction solution is preferably stirred during exposure to light, and cooled where appropriate.

Suitable solvents are those specified above.

In accordance with the invention, the organic compounds of the formula I can be used as photolatent bases.

Accordingly, the invention also provides for the use of a compound of the formula I

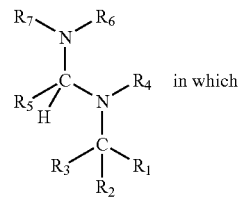

(I) in which $R_1$ is an aromatic or heteroaromatic radical which is capable of absorbing light in the wavelength range from 200 nm to 650 nm and is unsubstituted or is substituted one or more times by $C_1$-$C_{18}$alkyl, $C_2$-$C_{18}$alkenyl, $C_2$-$C_{18}$alkynyl, $C_1$-$C_{18}$haloalkyl, $NO_2$, $NR_{10}R_{11}$, CN, $OR_{12}$, $SR_{12}$, C(O)$R_{13}$, C(O)$OR_{14}$, halogen or a radical of formula II

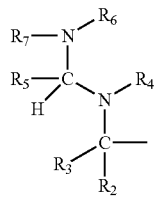

(II)

and which on absorption brings about a photoelimination which
leads to the generation of an amidine group;
$R_2$ and $R_3$ independently of one another are hydrogen, $C_1$-$C_{18}$alkyl or are phenyl which is unsubstituted or is substituted one or more times by $C_1$-$C_{18}$alkyl, CN, $OR_{12}$, $SR_{12}$, halogen or $C_1$-$C_{18}$haloalkyl;
$R_5$ is $C_1$-$C_{18}$alkyl or $NR_8R_9$;
$R_4$, $R_5$, $R_7$, $R_8$, $R_9$, $R_{10}$ and $R_{11}$ independently of one another are hydrogen or $C_1$-$C_{18}$alkyl; or
$R_4$ and $R_6$ together form a $C_2$-$C_{12}$alkylene bridge which is unsubstituted or is substituted by one or more $C_1$-$C_4$alkyl radicals; or
$R_5$ and $R_7$, independently of $R_4$ and $R_6$, together form a $C_2$-$C_{12}$alkylene bridge which is unsubstituted or is substituted by one or more $C_1$-$C_4$alkyl radicals; or
if $R_5$ is a radical $NR_8R_9$, $R_7$ and $R_9$ together form a $C_2$-$C_{12}$alkylene bridge which is unsubstituted or is substituted by one or more $C_1$-$C_4$alkyl radicals; and
$R_{12}$, $R_{13}$ and $R_{14}$ independently of one another are hydrogen or $C_1$-$C_{18}$alkyl;

as a photoinitiator for photochemically induced, base-catalysed polymerization, addition or substitution reactions.

The invention further provides a composition comprising
(A) at least one compound of the formula I

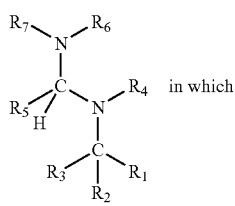

in which $R_1$ is an aromatic or heteroaromatic radical which is capable of absorbing light in the wavelength range from 200 nm to 650 nm and is unsubstituted or is substituted one or more times by $C_1$-$C_{18}$alkyl, $C_2$-$C_{18}$alkenyl, $C_2$-$C_{18}$alkynyl, $C_1$-$C_{18}$haloalkyl, $NO_2$, $NR_{10}R_{11}$, CN, $OR_{12}$, $SR_{12}$, C(O)$R_{13}$, C(O)$OR_{14}$, halogen or a radical of formula II

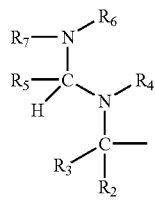

(II)

and which on absorption brings about a photoelimination which
leads to the generation of an amidine group;
$R_2$ and $R_3$ independently of one another are hydrogen, $C_1$-$C_{18}$alkyl or are phenyl which is unsubstituted or is substituted one or more times by $C_1$-$C_{18}$alkyl, CN, $OR_{12}$, $SR_{12}$, halogen or $C_1$-$C_{18}$haloalkyl;
$R_5$ is $C_1$-$C_{18}$alkyl or $NR_8R_9$;
$R_4$, $R_6$, $R_7$, $R_8$, $R_9$, $R_{10}$ and $R_{11}$ independently of one another are hydrogen or $C_1$-$C_{18}$alkyl; or
$R_4$ and $R_6$ together form a $C_2$-$C_{12}$alkylene bridge which is unsubstituted or is substituted by one or more $C_1$-$C_4$alkyl radicals; or
$R_5$ and $R_7$, independently of $R_4$ and $R_6$, together form a $C_2$-$C_{12}$alkylene bridge which is unsubstituted or is substituted by one or more $C_1$-$C_4$alkyl radicals; or
if $R_5$ is a radical $NR_8R_9$, $R_7$ and $R_9$ together form a $C_2$-$C_{12}$alkylene bridge which is unsubstituted or is substituted by one or more $C_1$-$C_4$alkyl radicals; and
$R_{12}$, $R_{13}$ and $R_{14}$ independently of one another are hydrogen or $C_1$-$C_{18}$alkyl;

and (B) at least one organic compound which is capable of a base-catalysed addition, condensation or substitution reaction or which is converted into a different form by a base-catalysed reaction.

The base-catalysed polymerization, addition, condensation or substitution reaction may be carried out with low molecular mass compounds (monomers), with oligomers, with polymeric compounds, or with a mixture of such compounds. Examples of reactions which can be conducted both on monomers and on oligomers/polymers using the photoinitiators of the invention are the Knoevenagel reaction and the Michael addition reaction. Where appropriate, the presence of further components, such as atmospheric humidity in the case of the base-catalysed crosslinking of acryloyloxysilanes or acyloxysilanes, is beneficial to or necessary for the reaction. This is disclosed, for example, in EP 1092757.

Of particular importance are compositions in which component (B) is an anionically polymerizable or crosslinkable organic material.

The organic material may be in the form of monofunctional or polyfunctional monomers, oligomers or polymers.

Particularly preferred oligomeric/polymeric systems are binders such as are customary in the coatings industry.

Examples of base-catalysable binders of this kind are:
a) acrylic copolymers with alkoxysilane and/or alkoxysiloxane side groups, examples being the polymers described in U.S. Pat. Nos. 4,772,672, 4,444,974 or EP 1092757;
b) two-component systems comprising hydroxyl-containing polyacrylates, polyesters and/or polyethers and aliphatic or aromatic polyisocyanates;
c) two-component systems comprising functional polyacrylates and polyepoxide, the polyacrylate containing thiol, amino, carboxyl and/or anhydride groups, as described, for example, in EP 898202;
d) two-component systems comprising fluorine-modified or silicone-modified, hydroxyl-containing polyacrylates, polyesters and/or polyethers and aliphatic or aromatic polyisocyanates;
e) two-component systems comprising (poly)ketimines and aliphatic or aromatic polyisocyanates;
f) two-component systems comprising (poly)ketimines and unsaturated acrylic resins or acetoacetate resins or methyl α-acrylamidomethylglycolate;
h) two-component systems comprising (poly)oxazolidines and polyacrylates containing anhydride groups or unsaturated acrylic resins or polyisocyanates;
i) two-component systems comprising epoxy-functional polyacrylates and carboxyl-containing or amino-containing polyacrylates;
l) polymers based on allyl glycidyl ether;

m) two-component systems comprising a (poly)alcohol and/or (poly)thiol and a (poly)isocyanate;

n) two-component systems comprising an α,β-ethylenically unsaturated carbonyl compound and a polymer containing activated $CH_2$ groups, the activated $CH_2$ groups being present either in the main chain or in the side chain or in both, as is described, for example, in EP 161697 for (poly)malonate groups. Other compounds containing activated $CH_2$ groups are (poly)acetoacetates and (poly)cyanoacetates.

o) Two-component systems comprising a polymer containing activated $CH_2$ groups, the activated $CH_2$ groups being present either in the main chain or in the side chain or in both, or a polymer containing activated $CH_2$ groups such as (poly)acetoacetates and (poly)cyanoacetates, and a polyaldehyde crosslinker, such as terephthalaldehyde. Such systems are described, for example, in Urankar et al., Polym. Prepr. (1994), 35, 933.

Within this group of base-catalysable binders, the following are particularly preferred:

b) two-component systems comprising hydroxyl-containing polyacrylates, polyesters and/or polyethers and aliphatic or aromatic polyisocyanates;

c) two-component systems comprising functional polyacrylates and a polyepoxide, the polyacrylate containing thiol, amino, carboxyl and/or anhydride groups;

i) two-component systems comprising epoxy-functional polyacrylates and carboxyl-containing or amino-containing polyacrylates;

m) two-component systems comprising a (poly)alcohol and/or (poly)thiol and a (poly)isocyanate, and n) two-component systems comprising an α,β-ethylenically unsaturated carbonyl compound and a polymer containing activated $CH_2$ groups, the activated $CH_2$ groups being present either in the main chain or in the side chain or in both.

Two-component systems comprising an α,β-ethylenically unsaturated carbonyl compound and a (poly)malonate and their preparation are described in EP 161687. The malonate group may either be attached in the main chain or in a side chain of a polyurethane, polyester, polyacrylate, epoxy resin, polyamide or polyvinyl polymer. The α,β-ethylenically unsaturated carbonyl compound can be any double bond activated by a carbonyl group. Examples are esters or amides of acrylic acid or methacrylic acid. In the ester groups it is also possible for there to be additional hydroxyl groups. Diesters and triesters are possible as well. Typical are, for example, hexanediol diacrylate or trimethylolpropane triacrylate. Instead of acrylic acid it is also possible to use other acids and their esters or amides, such as crotonic acid or cinnamic acid, for example.

The components of the system react with one another under base catalysis at room temperature to form a crosslinked coating system which is suitable for a large number of applications. Because of its already good weathering stability it is also suitable, for example, for exterior applications and can where necessary be further stabilized by UV absorbers and other light stabilizers.

Further suitable components (B) in the compositions of the invention include epoxy systems. Epoxy resins suitable for preparing curable mixtures of the invention comprising epoxy resin components B) are the epoxy resins which are customary in epoxy resin technology. Examples of such resins are:

Polyglycidyl esters and poly(β-methylglycidyl) ester, obtainable by reacting a compound having at least two carboxyl groups in the molecule with epichlorohydrin or β-methylepichlorohydrin, respectively. The reaction takes place appropriately in the presence of bases.

As the compound having at least two carboxyl groups in the molecule it is possible to use aliphatic polycarboxylic acids. Examples of such polycarboxylic acids are oxalic acid, succinic acid, glutaric acid, adipic acid, pimelic acid, suberic acid, azeleic acid or dimerized or trimerized linoleic acid. It is, however, also possible to use cycloaliphatic polycarboxylic acids, such as tetrahydrophthalic acid, 4-methyltetrahydrophthalic acid, hexahydrophthalic acid or 4-methylhexahydrophthalic acid. It is also possible for aromatic polycarboxylic acids to be used, such as phthalic acid, isophthalic acid or terephthalic acid.

Polyglycidyl ethers or poly-(β-methylglycidyl) ethers obtainable by reacting a compound containing at least two free alcoholic hydroxyl groups and/or phenolic hydroxyl groups with epichlorohydrin or β-methylepichlorohydrin, respectively, under alkaline conditions, or in the presence of an acidic catalyst with subsequent alkali treatment.

The glycidyl ethers of this type derive, for example, from acyclic alcohols, such as from ethylene glycol, diethylene glycol and higher poly(oxyethylene) glycols, propane-1,2-diol or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, pentaerythritol, sorbitol, and from polyepichlorohydrins. They also derive, however, for example, from cycloaliphatic alcohols, such as 1,4-cyclohexanedimethanol, bis(4-hydroxycyclohexyl)methane or 2,2-bis (4-hydroxycyclohexyl)propane, or possess aromatic nuclei, such as N,N-bis(2-hydroxyethyl)aniline or p,p'-bis(2-hydroxyethylamino)diphenylmethane. The glycidyl ethers may also derive from mononuclear phenols, such as from resorcinol or hydroquinone, for example, or are based on polynuclear phenols, such as bis(4-hydroxyphenyl)methane, 4,4'-dihydroxybiphenyl, bis(4-hydroxyphenyl) sulfone, 1,1,2,2-tetrakis(4-hydroxyphenyl)ethane, 2,2-bis(4-hydroxyphenyl) propane, 2,2-bis(3,5-dibromo-4-hydroxyphenyl)propane, and also from novolaks obtainable by condensation of aldehydes, such as formaldehyde, acetaldehyde, chloral or furfuraldehyde, with phenols, such as phenol, or with phenols substituted in a nucleus by chlorine atoms or $C_1$-$C_9$alkyl groups, such as 4-chlorophenol, 2-methylphenol, or 4-tert-butylphenol, or by condensation with bisphenols, those of the type specified above.

Poly(N-glycidyl) compounds obtainable by dehydrochlorinating the reaction products of epichlorohydrin with amines containing at least two amine hydrogen atoms. These amines are, for example, aniline, n-butylamine, bis(4-aminophenyl) methane, m-xylylenediamine or bis(4-methylaminophenyl) methane.

The poly(N-glycidyl) compounds also include, however, triglycidyl isocyanurate, N,N'-diglycidyl derivatives of cycloalkyleneureas, such as ethyleneurea or 1,3-propyleneurea, and diglycidyl derivatives of hydantoins, such as 5,5-dimethylhydantoin.

Poly-(S-glycidyl) compounds, examples being di-S-glycidyl derivatives deriving from dithiols, such as ethane-1,2-dithiol or bis(4-mercaptomethylphenyl) ether.

Cycloaliphatic epoxy resins, examples being bis(2,3-epoxycyclopentyl) ether, 2,3-epoxycyclopentyl glycidyl ether, 1,2-bis(2,3-epoxycyclopentyloxy)ethane and 3,4-epoxycyclohexylmethyl 3',4'-epoxycyclohexanecarboxylate.

It is, however, also possible to use epoxy resins where the 1,2-epoxide groups are attached to different heteroatoms and/or functional groups; these compounds include, for example, the N,N,O-triglycidyl derivative of 4-aminophenol, the glycidyl ether glycidyl ester of salicylic acid, N-glycidyl-N'-(2-glycidyloxypropyl)-5,5-dimethylhydantoin and 2-glycidyloxy-1,3-bis(5,5-dimethyl-1-glycidylhydantoin-3-yl) propane.

As component (B) it is also possible to use mixtures of epoxy resins. Also in accordance with the invention, therefore, are compositions comprising as component (B) an epoxy resin or a mixture of different epoxy resins.

The compositions contain the photoinitiator, component (A), in an amount, for example, of from 0.01 to 20% by weight, preferably from 0.01 to 10% by weight, based on component (B).

Component (B) may also comprise compounds which are converted into a different form by exposure to bases. These are, for example, compounds which under base catalysis alter their solubility in suitable solvents, by elimination of protective groups, for example. Examples are chemically amplified photoresist formulations which react under base catalysis, as described, for example, by Leung in Polym. Mat. Sci. Eng. 1993, 68, 30.

Further examples of suitable components (B) which are converted into a different form under base catalysis are given later on below in connection with the description of photoresist applications.

In addition to the photoinitiator, component A), the photopolymerizable mixtures may include various additives. Examples of these are thermal inhibitors which are intended to prevent premature polymerization, such as hydroquinone, hydroquinone derivatives, parahydroxytempo, p-methoxyphenol, β-naphthol or sterically hindered phenols such as 2,6-di(tert-butyl)-p-cresol, for example. To increase the dark storage stability it is possible, for example, to use copper compounds, such as copper naphthenate, stearate or octoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, such as N-diethyl-hydroxylamine or the ammonium or aluminium salt of N-nitrosophenylhydroxylamine, e.g. cupferron. To exclude atmospheric oxygen during polymerization it is possible to add paraffin or similar waxlike substances, which owing to their lack of solubility in the polymer migrate to the surface at the beginning of polymerization where they form a transparent surface layer which prevents the ingress of air. It is likewise possible to apply an oxygen-impermeable layer. Light stabilizers which can be added, in a small amount, are UV absorbers such as those, for example, of the hydroxyphenyl-benzotriazole, hydroxyphenylbenzophenone, oxalamide or hydroxyphenyl-s-triazine type. Individual compounds or mixtures of these compounds can be used, with or without the employment of sterically hindered amines (HALS).

Examples of such UV absorbers and light stabilizers are given below.

1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl) benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl -2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; transesterification product of 2-[3'-tert-butyl-5'-(2-methoxycarbonylethyl)-2'-hydroxyphenyl]benzotriazole with polyethylene glycol 300; [R—CH$_2$CH$_2$—COO(CH$_2$)$_3$]$_2$— where R=3-tert-butyl-4'-hydroxy -5'-2H-benzotriazol-2-ylphenyl.

2. 2-Hydroxybenzophenones, for example the 4-hydroxy, 4-methoxy-, 4-octoxy-, 4-decyloxy, 4-dodecyloxy, 4-benzyloxy, 4,2',4'-trihydroxy and 2'-hydroxy-4,4'-dimethoxy derivative.

3. Esters of substituted and unsubstituted benzoic acids, for example 4-tert-butylphenyl salicylate, phenyl salicylate, octylphenyl salicylate, dibenzoylresorcinol, bis(4-tert-butyl-benzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate and 2-methyl-4,6-di-tert-butylphenyl 3,5-di-tert-butyl-4-hydroxybenzoate.

4. Acrylates, for example ethyl or isooctyl α-cyano-β,β-diphenylacrylate, methyl α-carbomethoxycinnamate, methyl and butyl α-cyano-β-methyl-β-methoxycinnamate, methyl α-carbomethoxy-p-methoxycinnamate and N-(β-carbomethoxy-β-cyanovinyl)-2-methylindoline.

5. Sterically hindered amines, such as bis(2,2,6,6-tetramethylpiperidyl) sebacate, bis(2,2,6,6-tetramethylpiperidyl) succinate, bis(1,2,2,6,6-pentamethylpiperidyl) sebacate, bis (1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro-[4.5]-decane-2,4-dione, bis(1-octyloxy-2,2,6,6-tetramethylpiperidyl) sebacate, bis(1-octyloxy-2,2,6,6-tetramethylpiperidyl) succinate, condensation product of N,N'-bis(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis(3-aminopropylamino)ethane, condensation product of 2-chloro-4,6-di-(4-n-butylamino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-di-dodecyloxy-5,5'di-tert-butyloxanilide, 2-ethoxy-2'-ethyloxanilide, N,N'-bis(3-dimethylaminopropyl) oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl-4,6-bis(2,4-dimethylphenyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-(2-hydroxypropoxy-2-hydroxyphenyl]4,6-bis(2,4-dimethylphenyl)-1,3,5-triazine, 2-[2-hydroxy-4-(2-hydroxy-3-dodecyloxypropoxy)phenyl]4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2{-2-hydroxy-4-[3-(2-ethylhexyl-1-oxy)-2-hydroxypropyloxy]phenyl}1,6-bis (2,4-dimethylphenyl)-1,3,5-triazine.

8. Phosphites and phosphonites, for example, triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl) pentaerythritol diphosphite, bisisodecyloxy pentaerythritol diphosphite, bis(2,4-di-tert-butyl-6-methylphenyl) pentaerythritol diphosphite, bis(2,4,6-tri-tert-butylphenyl) pentaerythritol diphosphite, tristearyl sorbitol triphosphite, tetrakis(2,4-di-tert-butylphenyl)4,4'-biphenylenediphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-12-methyldibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite.

Examples of further additives are:

Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibres of other natural products, synthetic fibres. Other additives, for example plasticizers, lubricants, emulsifiers, pigments, rheological additives, catalysts, levelling assistants, optical brighteners, flameproofing agents, antistatics, blowing agents.

In addition to the additives indicated above it is also possible for additional coinitiators or sensitizers to be present. In general these are aromatic ketones or dyes which improve the overall quantum yield by means, for example, of energy transfer or electron transfer. Examples of suitable dyes which can be added as coinitiators are triarylmethanes, for example malachite green, indolines, thiazines, for example methylene blue, xanthones, thioxanthones, oxazines, acridines or phenazines, for example safranine, and rhodamines of the formula

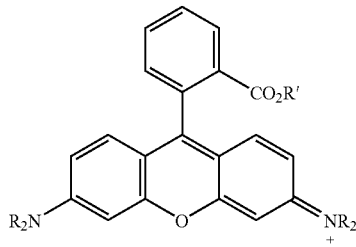

in which R is alkyl or aryl and R' is hydrogen or an alkyl or aryl radical, for example Rhodamine B, Rhodamine 6 G or Violamine R, and also Sulforhodamine B or Sulforhodamine G. Likewise suitable are fluorones such as, for example, 5,7-diiodo-3 butoxy-6-fluorone.

The invention further provides a composition as described above comprising in addition to components (A) and (B) a sensitizer (C).

Preferred components (C) are aromatic ketones, such as substituted or unsubstituted benzophenones, thioxanthones, anthraquinones or dyes such as oxazines, acridines, phenazines and rhodamines.

Likewise suitable in this context are combinations of dyes with borates, as are described, for example, in U.S. Pat. No. 4,772,530, GB 2 307 474, GB 2 307 473, GB 2 307 472 and EP 775 706.

Particular preference is given to substituted benzophenones or thioxanthones. Examples of suitable benzophenones are benzophenone, 4,4'-bis(dimethylamino)benzophenone, 4,4'-bis(diethylamino)benzophenone, 4,4'-bis(ethylmethylamino)benzophenone, 4,4'-diphenylbenzophenone, 4,4'-diphenoxybenzophenone, 4,4'-bis(p-isopropylphenoxy)benzophenone, 4-methylbenzophenone, 2,4,6-trimethylbenzophenone, 4-phenylbenzophenone, 2-methoxycarbonylbenzophenone, 4-benzoyl-4'-methyldiphenyl sulfide, 4-methoxy-3,3'-methylbenzophenone, isopropylthioxanthone, chlorothioxanthone, 1-chloro-4-propoxythioxanthone, 2,4-dimethylthioxanthone, 2,4-diethylthioxanthone, 1,3-dimethyl-2-(2-ethylhexyloxy) thioxanthone.

Likewise preferred are mixtures of benzophenones and/or thioxanthones such as, for example, a mixture of benzophenone and 4-methylbenzophenone or of 4-methylbenzophenone and 2,4,6-trimethylbenzophenone.

Further examples of such photosensitizers (C), which can be used either individually or as a mixture, are 1. Thioxanthones Thioxanthone, 2-isopropylthioxanthone, 3-isopropylthioxanthone, 2-chlorothioxanthone, 3-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di-[2-(2-methoxyethoxy)ethoxycarbonyl]thioxanthone, 1-ethoxycarbonyl-3-(1-methyl-1-morpholinoethyl)thioxanthone, 2-methyl-6-dimethoxymethylthioxanthone, 2-methyl-6-(1,1- dimethoxybenzyl)thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)thioxanthone-3,4-dicarboximide, 1-phenoxythioxanthone, 8-ethoxycarbonyl-2-methoxythioxanthone, 6-ethoxycarbonyl-2-methylthioxanthone, thioxanthone 2-polyethylene glycol esters, 2-hydroxy-3-(3,4-dimethyl-9-oxo-9H-thioxanthon-2-yloxy)-N,N,N-trimethyl-1-propanaminium chloride;

2. Benzophenones

Benzophenone, 4-phenylbenzophenone, 4-methoxybenzophenone, 4,4'-dimethoxybenzophenone, 4,4'-dimethylbenzophenone, 4,4'-dichlorobenzophenone, 4,4'-dimethylaminobenzophenone, 4,4'-diethylaminobenzophenone, 4-methylbenzophenone, 2,4,6-trimethylbenzophenone, 4-(4-methylthiophenyl)benzophenone, 3,3'-dimethyl-4-methoxybenzophenone, methyl-2-benzoylbenzoate, 4-(2-hydroxyethylthio)benzophenone, 4-(4-tolylthio)benzophenone, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)benzophenone, 4-benzoyl-N,N-dimethyl-N-[2-(1-oxo-2-propenyl)oxy]ethylbenzenemethanaminium chloride;

3. 3-Acylcoumarins 3-Benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonylbis[5,7-di(propoxy)coumarin], 3,3'-carbonylbis(7-methoxycoumarin), 3,3'-carbonylbis(7-diethylaminocoumarin), 3-isobutyroylcoumarin, 3-benzoyl-5,7-dimethoxycoumarin, 3-benzoyl-5,7-diethoxycoumarin, 3-benzoyl-5,7-dibutoxycoumarin, 3-benzoyl-5,7-di(methoxyethoxy)coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)coumarin, 5,7-dimethoxy-3-(1-naphthoyl)coumarin, 3-benzoylbenzo[f]coumarin, 7-diethylamino-3-thienoylcoumarin, 3-(4-cyanobenzoyl)-5,7-dimethoxycoumarin;

4. 3-(Aroylmethylene)thiazolines
3-Methyl-2-benzoylmethylene-β-naphthothiazoline, 3-methyl-2-benzoylmethylenebenzothiazoline, 3-ethyl-2-propionylmethylene-,β-naphthothiazoline;

5. Other Carbonyl Compounds

Acetophenone, 3-methoxyacetophenone, 4-phenylacetophenone, benzil, 2-acetylnaphthalene, 2-naphthaldehyde, 9,10-anthraquinone, 9-fluorenone, dibenzosuberone, xanthone, 2,5-bis(4-diethylaminobenzylidene)cyclopentanone, α-(para-dimethylaminobenzylidene) ketones, such as 2-(4-dimethylaminobenzylidene)indan-1-one or 3-(4-dimethylaminophenyl)-1-indan-5-yl-propenone, 3-phenylthiophthalimide, N-methyl-3,5-di(ethylthio)phthalimide.

In addition to the above-described base-catalysable (curable) binders, component B), the composition may also include other binders as well. Further olefinically unsaturated compounds, for example, are possible. The unsaturated compounds may include one or more olefinically double bonds. They may be of low molecular mass (monomeric) or higher molecular mass (oligomeric). Examples of monomers having a double bond are alkyl or hydroxyalkyl acrylates or methacrylates, such as methyl, ethyl, butyl, 2-ethylhexyl or 2-hydroxyethyl acrylate, isobornyl acrylate, methyl methacrylate or ethyl methacrylate. Silicone acrylates are also of interest. Further examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers having two or more double bonds are the diacrylates of ethylene glycol, propylene glycol, neopentyl glycol, hexamethylene glycol or bisphenol A, 4,4'-bis(2-acryloyloxyethoxy)diphenylpropane, trimethylolpropane triacrylate, pentaerythritol triacrylate or tetraacrylate, vinyl acrylate, divinyl benzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylated epoxy resins, acrylated polyesters or polyesters containing vinyl ether groups or epoxy groups, polyurethanes and polyethers. Further examples of unsaturated oligomers are unsaturated polyester resins which are mostly prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. In particular, combinations of vinyl ether-functional oligomers and polymers as are described in WO 90/01512 are very suitable. Also suitable, however, are copolymers of vinyl ether and maleic acid functionalized monomers. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

If, in addition, use is made of such free-radically curable monomers, oligomers/polymers then it is judicious to add a further photoinitiator which dissociates into free radicals. Such photoinitiators are known and are produced industrially. Examples are benzophenone, benzophenone derivatives, acetophenone, acetophenone derivatives, for example α-hydroxycycloalkyl phenyl ketones, especially α-hydroxycyclohexyl phenyl ketone or 2-hydroxy-2-methyl-1-phenylpropanone, dialkoxyacetophenones, α-hydroxy- or α-aminoacetophenones, such as (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers and benzil ketals, such as benzil dimethyl ketal, phenylglyoxalates and derivatives thereof, dimeric phenylglyoxalates, monoacylphosphine oxides, such as (2,4,6-trimethylbenzoyl)phenylphosphine oxide, bisacylphosphine oxides, such as bis(2,6-dimethoxybenzoyl)(2,4,4-trimethylpent-1-yl)phosphine oxide, bis(2,4,6-trimethylbenzoyl)phenylphosphine oxide or bis(2,4,6-trimethylbenzoyl)(2,4-dipentoxyphenyl)phosphine oxide, trisacylphosphine oxides, oxime esters, ferrocenium compounds or titanocenes, such as dicyclopentadienylbis(2,6-difluoro-3-pyrrolophenyl)titanium, for example.

Examples are specified in EP-A-284 561. Polymer systems of this kind, in which curing/crosslinking takes place by different mechanisms, are also referred to as hybrid systems.

The compositions of the invention can also have added to them non-reactive binders, which is particularly judicious if the photopolymerizable compounds are liquid or viscous substances. The amount of the non-reactive binder can be, for example, 5-95%, preferably 10-90% and, in particular, 40-90% by weight, based on the overall solids content. The choice of non-reactive binder is made in accordance with the field of use and with the properties required for this use, such as the possibility for development in aqueous and organic solvent systems, adhesion to substrates, and sensitivity to oxygen.

Examples of suitable binders are polymers having a molecular weight of around 5000-2,000,000, preferably 10,000-1,000,000. Examples are: homo- and copolymeric acrylates and methacrylates, for example copolymers of methyl methacrylate/ethyl acrylate/methacrylic acid, poly (alkyl methacrylates), poly(alkyl acrylates); cellulose esters and ethers, such as cellulose acetate, cellulose acetate butyrate, methylcellulose, ethylcellulose; polyvinylbutyral, polyvinylformal, cyclized rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/ vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide) and polyesters such as poly(ethylene glycol terephtalate) and poly (hexamethylene glycol succinate).

The invention additionally provides a process for carrying out base-catalysed reactions which comprises subjecting a composition according to claim 8 to irradiation with light having a wavelength of from 200 nm to 650 nm.

In some cases it may be advantageous to carry out heating during or after exposure to light. In this way it is possible in many cases to accelerate the crosslinking reaction.

Also in accordance with the invention are the use of compounds of the formula I for preparing coatings, moulding compounds or photostructured layers, and the process described above for preparing coatings, moulding compounds or photostructured layers.

The invention additionally provides a coated substrate coated on at least one surface with a composition as described above, and also a process for photographically producing relief images, in which a coated substrate is subjected to imagewise exposure and then the unexposed portions are removed with a solvent. Of particular interest here is the above-mentioned exposure to light by means of a laser beam.

A further subject of the invention is a polymerized or crosslinked composition as described above.

The sensitivity of the novel compositions to light generally extends from about 200 nm through the UV region and into the infrared region (about 20,000 nm, in particular 1200 nm) and therefore spans a very broad range. Suitable radiation comprises, for example, sunlight or light from artificial light sources. Therefore, a large number of very different types of light source can be used. Both point sources and flat radiators (lamp carpets) are suitable. Examples are carbon arc lamps, xenon arc lamps, medium-pressure, high-pressure and low-pressure mercury lamps, doped if desired with metal halides (metal halogen lamps), microwave-stimulated metal vapour lamps, excimer lamps, superactinic fluorescent tubes, fluorescent lamps, incandescent argon lamps, electronic flashlights, xenon flashlights, photographic flood lamps, electron beams and X-rays, produced by means of synchrotrons or laser plasma. The distance between the lamp and the substrate according to the invention which is to be exposed can vary depending on the application and on the type and/or power of the lamp, for example between 2 cm and 150 cm. Also especially suitable are laser light sources, for example excimer lasers. Lasers in the visible region or in the IR region can also be employed. Very advantageous here is the high sensitivity of the novel materials and the possibility of adapting the absorption wavelength to the laser line by using a dye as coinitiator. By this method it is possible to produce printed circuits in the electronics industry, lithographic offset printing plates or relief printing plates, and also photographic image recording materials.

Depending on the light source used it is advantageous in many cases to employ a sensitizer, as described above, whose absorption spectrum coincides as closely as possible to the emission spectrum of the radiation source.

The compositions of the invention can be employed for various purposes, for example as printing inks, as clearcoats, as white paints, for example for wood or metal, as coating materials, inter alia for paper, wood, metal or plastic, as powder coatings, as daylight-curable exterior coatings for marking buildings and roads, for photographic reproduction processes, for holographic recording materials, for image recording processes or for the production of printing plates which can be developed using organic solvents or aqueous-alkaline media, for the production of masks for screen printing, as dental filling materials, as adhesives, including pressure-sensitive adhesives, as laminating resins, as etch resists or permanent resists and as solder masks for electronic circuits, for the production of three-dimensional articles by mass curing (UV curing in transparent moulds) or by the stereolithography process, as is described, for example, in U.S. Pat. No. 4,575,330, for the preparation of composite materials (for example styrenic polyesters, which may contain glass fibres and/or other fibres and other assistants) and other thick-layer compositions, for the coating or encapsulation of electronic components, or as coatings for optical fibres.

Of particular interest is the use of the compositions of the invention for preparing decorative coatings, such as exterior coatings on substrates of all kinds, for example buildings, fences, chipboard panels, and as a coating on stone, concrete or metal, for the coating of vehicles, for example, such as cars, railways or aircraft. The compositions may likewise be used in automotive OEM finishing and automotive refinish, and also for the finishing of car bodies, plastic parts for cars and body-mounted car parts. The initiators of the invention can be used in a multicoat system in the surfacer, base coat or clearcoat. Their use in pigmented topcoats is also possible.

In surface coatings, it is common to use mixtures of a prepolymer with polyunsaturated monomers which also contain a monounsaturated monomer. The prepolymer here is primarily responsible for the properties of the coating film, and varying it allows the skilled worker to influence the properties of the cured film. The polyunsaturated monomer functions as a crosslinker, which renders the coating film insoluble. The monounsaturated monomer functions as a reactive diluent, by means of which the viscosity is reduced without the need to use a solvent.

The photocurable compositions of the invention are suitable, for example, as coating materials for substrates of all kinds, examples being wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, on which it is the intention to apply a protective coating or, by imagewise exposure, an image.

The substrates can be coated by applying a liquid composition, a solution or suspension to the substrate. The choice of solvent and the concentration depend predominantly on the type of composition and the coating process. The solvent should be inert: in other words, it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

Using known coating processes, the solution is applied uniformly to a substrate, for example by spin coating, dip coating, knife coating, curtain coating, brushing, spraying—especially electrostatic spraying—and reverse roll coating and by electrophoretic deposition. It is also possible to apply the photosensitive layer to a temporary, flexible support and then to coat the final substrate, for example a copper-clad circuit board, by means of layer transfer via lamination.

The amount applied (layer thickness) and the nature of the substrate (layer support) are functions of the desired field of application. The range of layer thicknesses generally comprises values from about 0.1 µm to more than 100 µm.

The radiation-sensitive compositions of the invention can also be subjected to imagewise exposure. In this case they are used as negative resists. They are suitable for electronics (galvanoresists, etch resists and solder resists), for the production of printing plates, such as offset printing plates, flexographic and relief printing plates or screen printing plates, for the production of marking stamps, and can be used for chemical milling or as microresists in the production of integrated circuits. There is a correspondingly wide range of variation in the possible layer supports and in the processing conditions of the coated substrates.

Where the radiation-sensitive compositions of the invention are resins which are converted from a water-insoluble form into a water-soluble form under the influence of the photochemically liberated amine, they can be used as positive resists on imagewise exposure to light. Examples of such resins are polystyrene resins containing benzisoxazol and phenol groups, as described by Niu et al. in J. Polym. Mater. Sci. Eng. (1996), 75, 427, or polyhydroxystyrene resins some or all of whose hydroxyl groups have been protected by carbonate groups which can be eliminated under base catalysis, as described, for example, by Urankar et al. in Macromolecules (1997), 30, 1304.

The term "imagewise" exposure relates both to exposure through a photomask containing a predetermined pattern, for example a slide, exposure by a laser beam which is moved under computer control, for example, over the surface of the coated substrate and so generates an image, and irradiation with computer-controlled electron beams.

Following the imagewise exposure of the material and prior to developing, it may be advantageous to carry out a brief thermal treatment, in which only the exposed parts are thermally cured. The temperatures employed are generally 50-150° C. and preferably 80-130° C.; the duration of the thermal treatment is generally between 0.25 and 10 minutes.

A further field of use for photocuring is that of metal coating, for example the surface-coating of metal panels and tubes, cans or bottle tops, and photocuring on polymer coatings, for example of floor or wall coverings based on PVC.

Examples of the photocuring of paper coatings are the colourless varnishing of labels, record sleeves or book covers.

The use of the compounds of the invention for curing shaped articles made from composite compositions is likewise of interest. The composite composition is made up of a self-supporting matrix material, for example a glass-fibre fabric, or else, for example, of plant fibres [cf. K.-P. Mieck, T. Reussmann in Kunststoffe 85 (1995), 366-370], which is impregnated with the photocuring formulation. Shaped articles which are produced from composite compositions using the compounds according to the invention are of high mechanical stability and resistance. The compounds of the invention can also be used as photocuring agents in moulding, impregnating and coating compositions, as are described, for example, in EP-A-7086. Examples of such compositions are fine coating resins on which stringent requirements are placed with respect to their curing activity and resistance to yellowing, or fibre-reinforced mouldings such as planar or longitudinally or transversely corrugated light diffusing panels.

The examples which follow illustrate the invention, without wishing to restrict it to the examples. As in the remainder of the description and in the claims, parts and percentages are by weight unless indicated otherwise. If alkyl radicals having more than three carbon atoms are referred to without any indication of the isomer involved, then it is always the n-isomer which is meant.

EXAMPLE 1

Preparation of
5-benzyl-1,5-diazabicyclo[4.3.0]nonane

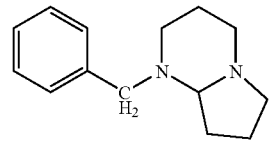

1.1: 1,5-Diazabicyclo[4.3.0]nonane

A 2.5 l sulfonating flask is charged with 125 g (1 mol) of 1,5-diaza[4.3.0]non-5-ene in 1470 ml of tert-butyl methyl ether. Thereafter, in portions, 18.97 g (0.5 mol) of lithium aluminium hydride are introduced into the solution and the resulting emulsion is stirred at room temperature for an hour. The reaction mixture is subsequently warmed to 55-57° C. over two hours and is stirred to completion at room temperature overnight. After that time, according to thin-layer chromatography, the starting material has undergone complete reaction. The reaction mixture is cooled to 0° C. and, carefully, 19 ml of water and then 19 ml of 10% strength sodium hydroxide solution are added. Finally, a further 57 ml of water are added. After the mixture has been stirred for an hour it is filtered over Hyflo and the product on the suction filter is washed with 200 ml of tert-butyl methyl ether and with twice 200 ml of methylene chloride. The combined organic phases are dried over sodium sulfate and the solvent is distilled off on a rotary evaporator. This gives 105.99 g of 1,5-diaza[4.3.0] nonane as a yellowish oil.

For further purification, the crude product is distilled at 47-53 mbar using a Vigreux column. The fractions which go over at 82-85° C. contain the pure product. Yield: 89.13 g (75%) of 1,5-diaza[4.3.0]nonane as a colourless oil.

$^1$H NMR ($d_6$-DMSO) [ppm]: 3.5 (broad signal NH); 3.05-3.0 (1H, m), 3.0-2.9 (m, 1H), 2.9-2.8 (m, 2H), 2.7-2.6 (m, 1H), 2.05-1.95 (m, 1H); 1.85-1.45 (m, 5H); 1.4-1.35 (m, 2H).

1.2: 5-Benzyl-1,5-diazabicyclo[4.3.0]nonane

In a 750 ml sulfonating flask, 21.0 g (0.525 mol) of sodium hydroxide and 5.81 g of potassium iodide (0.035 mol) are suspended in 350 ml of dichloromethane. Then 44.31 g (0.35 mol) of benzyl chloride and 44.71 g (0.35 mol) of 5-benzyl-1,5-diaza[4.3.0]nonane are added and the suspension is stirred at room temperature. After 24 hours, the signal of the benzylic protons in benzyl chloride in the $^1$HNMR is no longer visible. The reaction mixture is poured out into 200 ml of water. The organic phase is separated off in a separating funnel and then the solvent is stripped off on a rotary evaporator. The yellowish liquid which remains has 500 ml of hexane added to it. Precipitated salts are removed by filtration and the solvent is distilled off on a rotary evaporator. This gives 43.07 g of 5-benzyl-1,5-diazabicyclo-[4.3.0]nonane as a pale yellowish oil which slowly solidifies on standing.

For further purification, the crude product is distilled under reduced pressure (p=$10^{-1}$ mbar) on a Vigreux column. The fractions which go over at 129-136° C. contain the desired product and are combined. There are 26.2 g of colourless 5-benzyl-1,5-diazabicyclo[4.3.0]nonane, which crystallize out on cooling. The melting point of the product is 38-40° C.

Elemental analysis calculated for $C_{14}H_{20}N_2$:

| calculated: | C 77.73% | H 9.32% | N 12.95% |
| --- | --- | --- | --- |
| found: | C 77.49% | H 9.38% | N 12.97% |

$^1$H NMR ($d_6$-DMSO) [ppm]: 7.35-7.15 (5H, m, ArH), 3.80 (d, J=15 Hz, 1H PhC$\underline{H}_2$N═), 3.04 (1H, d, J=15 Hz, PhC$\underline{H}_2$N═), 3.0-2.9 (m, 2H), 2.75-2.65 (m, 1H, H—C(6)), 2.45-2.3 (m, 1H), 2.25-2.05 (m, 1H); 2.05-1.55 (m, 7H), 1.4-1.3 (m, 1H).

EXAMPLE 2

Preparation of 5-(anthracen-9-yl-methyl)-1,5-diaza[4.3.0]nonane

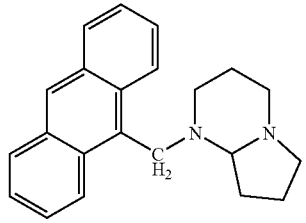

The compound of Example 2 is prepared by the procedure specified for Example 1 using 9-chloromethylanthracene instead of benzyl chloride. The product is obtained as a yellowish solid.

Elemental analysis calculated for $C_{22}H_{24}N_2$:

| calculated: | C 83.50% | H 7.64% | N 8.85% |
| --- | --- | --- | --- |
| found: | C 83.00% | H 7.93% | N 8.73% |

$^1$H NMR ($d_6$-DMSO) [ppm]: 8.58 (d, J=8, 2 ArH); 8.57 (s, 1 ArH); 8.08 (d, J=8, 2 ArH); 7.55-7.45 (m, 4 ArH); 4.6 (d, J=15 Hz, 1H PhC$\underline{H}_2$N═), 4.25 (1H, d, J=15 Hz, PhC$\underline{H}_2$N═), 3.05-2.85 (m, 3H), 2.7-2.9 (m, $_1$H, H—C(6)), 2.3-1.6 (m, 8H), 1.25-1.23 (m, 1H).

EXAMPLE 3

Preparation of 5-(2'-nitrobenzyl)-1,5-diazabicyclo [4.3.0]nonane

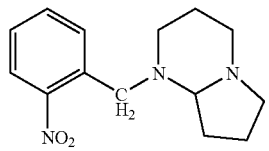

In a 350 ml sulfonating flask, 2.80 g of 2,2,6,6-tetramethylpiperidine (19.8 mmol) are added to a solution of 2.50 g of 1,5-diaza[4.3.0]nonane (prepared as described under 1.1) in toluene (60 ml). Then 4.28 g of 2-nitrobenzyl bromide (19.8 mmol) in toluene (50 ml) are slowly added dropwise and the solution is stirred at room temperature. After 17 hours, the reaction mixture is filtered over Hyflo. The filtrate is washed with water and dried over magnesium sulfate. Filtration, evaporation of the solvent and chromatography (mobile phase: 9:1 acetone/methanol) give 5-(2'-nitrobenzyl)-1,5-diazabicyclo[4.3.0]nonane (3.66 g, 71%) as a brown solid.

$^1$H NMR (CDCl$_3$) [ppm]: 7.82 (2H, m, ArH), 7.50 (1H, m, ArH), 7.30 (1H, m, ArH), 4.11 (d, J=16 Hz, 1H PhC$\underline{H}_2$N═), 3.40 (1H, d, J=16 Hz, PhC$\underline{H}_2$N═), 3.06 (m, 2H), 2.72 (m, 1H), 2.53 (m, 1H), 2.28-2.01 (m, 2H); 1.96-1.75 (m, 4H); 1.70-1.41 (m, 2H); 1.17 (m, 1H).

EXAMPLE 4

Preparation of 5-(4'-cyanobenzyl)-1,5-diazabicyclo [4.3.0]nonane

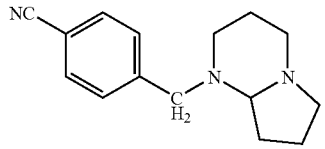

In a 1 l three-necked flask, 18.19 g (0.09 mol) of 4-(bromomethyl)benzonitrile are dissolved in 480 ml of acetonitrile, and 12.44 g (0.09 mol) of potassium carbonate and a spatula tip of potassium iodide are added to the solution. The resulting suspension is slowly admixed dropwise with stirring at room temperature with 11.4 g (0.09 mol) of 1,5-diaza [4.3.0]nonane (prepared as described under 1.1). The reaction mixture is stirred overnight and then filtered. Removal of the solvent by distillation on a rotary evaporator gives a viscous brown oil. By multiple extraction of this oil with tert-butyl methyl ether, it yields pure 5-(4'-cyanobenzyl)-1,5-diazabicyclo[4.3.0]nonane as an amorphous orange solid.

Elemental analysis calculated for $C_{15}H_{19}N_3$:

| calculated: | C 74.65% | H 7.94% | N 17.41% |
| --- | --- | --- | --- |
| found: | C 74.29% | H 8.00% | N 16.63% |

$^1$H NMR (CDCl$_3$) [ppm]: 7.61 (d, J=10 Hz, 2 ArH, H—C (2') and H—C(6')); 7.52 (d, J=10 Hz, 2 ArH, H—C(3') and H—C(5')); 3.94 (d, J=15, 1H PhC$\underline{H}_2$N═), 3.17 (d, J=15, 1H PhC$\underline{H}_2$N═), 3.15-3.05 (m, 2H), 2.85-2.75 (m, 1H, H—C(6)), 2.5-2.40 (m, 1H)); 2.35-2.215 (m, 1H); 2.15-1.6 (m, 7H); 1.5-1.4 (m, 1H).

EXAMPLES 5-6

Examples 5 and 6 below are carried out using the method described for Example 4 but employ in the corresponding aralkyl bromides R—Br instead of 4-(bromomethyl)benzonitrile. The compounds and their physical data are reproduced in Table 1.

TABLE 1

| Example | Ar | Name and analytical data<br>1H NMR[ppm]/Elemental analysis [%] |
|---|---|---|
| 5 | 3-cyanophenyl | 5-(3'-Cyanobenzyl)-1,5-diazabicyclo[4.3.0]nonane<br>Orange solid<br>$^1$HNMR(CDCl$_3$): 7.7(s, 1ArH, H—C(2')); 7.63(d, J=8Hz, 1ArH, H—C(4')); 7.52(d, J=8Hz, 1ArH ,H—C(6')); 7.40(t, J=8Hz, 1ArH, H—C(5')); 3.92(d, J=15, 1H PhCH$_2$N=), 3.14(d, J=15, 1H PhCH$_2$N=), 3.15-3.05(m, 2H), 2.85-2.75(m, 1H, H—C(6)), 2.5-2.45(m, 1H)); 2.3-2.15(m, 1H); 2.1-1.6(m, 7H); 1.55-1.45(m, 1H)<br>Elemental analysis calculated for C$_{15}$H$_{19}$N$_3$:<br>calc.: C 74.65  H 7.94  N 17.41<br>found: C 74.43  H 7.95  N 17.41 |
| 6 | anthraquinon-2-yl | 5-(anthraquinon-2-yl-methyl)-1,5-diaza[4.3.0]nonane<br>Hygroscopic orange solid<br>$^1$H NMR(d$_6$-DMSO): 8.25-8.25-8.05(m, 4ArH); 7.95-7.9(m, 2ArH); 7.85-7.8(m, 1ArH); 3.93(d, J=15, 1H PhCH$_2$N=), 3.42(d, J=15, 1H PhCH$_2$N=), 3.05-2.95(m, 2H), 2.75-2.65(m, 1H, H—C(6)), 2.6-2.5(m, 1H)); 2.2-1.9(m, 4H); 1.75-1.5(m, 43H); 1.4-1.35(m, 1H) |

EXAMPLE 7

Preparation of 5-(2'-chlorobenzyl)-1,5-diazabicyclo[4.3.0]nonane

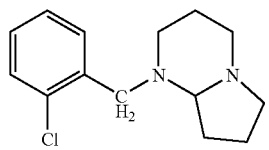

In a 250 ml three-necked flask, 5 g (0.04 mol) of 1,5-diazabicyclo[4.3.0]non-5-ene are dissolved in 100 ml of tetrahydrofuran, and at room temperature 6.48 g (0.04 mol) of 2-chlorobenzyl chloride are slowly added with stirring. A colourless suspension is formed which is stirred overnight. The suspension is then filtered, the salt isolated by filtration is washed, and the washed salt is suspended in 100 ml of tetrahydrofuran. Added to this suspension in portions is 0.76 g (0.02 mol) of lithium aluminium hydride. After the end of the addition, the reaction mixture is stirred at room temperature overnight. It is then cooled to 0° C. and, dropwise, 0.8 g of water, then 0.8 g of 10% strength sodium hydroxide solution and a further 2.4 g of water are added. The resulting suspension is stirred at room temperature for 30 minutes and then filtered. The filter cake is washed with tetrahydrofuran and the combined organic phases are dried and concentrated on a rotary evaporator. This gives 7.15 g of 5-(2-chlorobenzyl)-1,5-diazabicyclo[4.3.0]nonane as a colourless oil.

Elemental analysis calculated for C$_{14}$H$_{19}$ClN$_2$:

| | | | |
|---|---|---|---|
| calculated: | C 67.05% | H 7.64% | N 11.17% |
| found: | C 66.95% | H 7.84% | N 10.90% |

$^1$H NMR (d$_6$-DMSO) [ppm]: 7.51 (d, J=7.5 Hz, 1H, ArH (C(3')), 7.41 (d, J=7.5 Hz, 1H, ArH (C(4')), 7.35-7.25 (m, 3H, ArH), 3.79 (1H, d, J=15 Hz, PhCH$_2$N=), 3.27 (1H, d, J=15 Hz, PhCH$_2$N=), 3.0-2.9 (m, 2H), 2.8-2.7(m, 1H) 2.6-2.5 (m, 1H), 2.2-2.1 (m, 2H); 2.10-1.3 (m, 6H).

EXAMPLES 8-13

Examples 8-13 below are carried out by the method described in Example 7, using in each case the corresponding aralkyl chloride Ar—CH$_2$—Cl instead of 2-chlorobenzyl chloride. The compounds and their physical data are listed in Table 2.

TABLE 2

| Example | Ar | Name and analytical data<br>1H NMR[ppm]/Elemental analysis[%] |
|---|---|---|
| 8 | H₃C—(4-phenyl) | 5-(4'-Methylbenzyl)-1,5-diazabicyclo[4.3.0]nonane<br>Colourless crystals, m.p. 44° C.<br>$^1$H NMR($d_6$-DMSO): 7.16 and 7.09(two d, each two H, ArH on C(2', 3', 5' and 6'); 3.75(d, J=15, 1H PhCH$_2$N=), 2.94(d, J=15, 1H PhCH$_2$N=), 3.0-2.9(m, 2H), 2.75-2.65 (m, 1H, H—C(6)), 2.45-2.35(m, 1H), 2.27(s, 3H, CH$_3$—Ar); 2.2-2.15(m, 1H); 2.05-1.85(m, 2H), 1.8-1.55(m, 5H) and 1.4-1.3(m, 1H)<br>Elemental analysis calculated for C$_{15}$H$_{22}$N$_2$:<br>calc.:  C 78.21   H 9.63   N 12.16<br>found: C 78.11   H 9.68   N 12.04 |
| 9 | 2,4,6-trimethylphenyl | 5-(2',4',6'-Trimethylbenzyl)-1,5-diazabicyclo[4.3.0]nonane<br>Colourless oil<br>$^1$H NMR($d_6$-DMSO): 6.78(s, 2ArH C(3' and C(5')); 3.62 (d, J=10, 1H PhCH$_2$N=), 3.11(d, J=10, 1H PhCH$_2$N=); 2.95-2.85(m, 2H), 2.55-2.5(m, 1H), 2.45-2.35(m, 1H, H—C(6)), 2.30(s, 6H, CH$_3$—C(2') and CH$_3$—C(6'); 2.2-2.1(m, 1H); 2.18(s, 3H, CH$_3$—C(4'); 2.05-1.95(m, 1H)1.85-1.45 (m, 6H); 1.4-1.3(m, 1H)<br>Elemental analysis for C$_{17}$H$_{26}$N$_2$:<br>calc.:  C 79.02   H 10.14   N 10.84<br>found: C 78.25   H 10.26   N 10.47 |
| 10 | 4-ethenylphenyl | 5-(4'-Ethenylbenzyl)-1,5-diazabicyclo[4.3.0]nonane<br>Yellowish oil<br>$^1$H NMR($d_6$-DMSO): 7.41(d, 2ArH); 7.25(d, 2ArH); 6.69 (dxd, J$_{trans}$ = 15, J$_{cis}$ = 8, 1H, H—C(7'); 6.8(d, J$_{trans}$ = 15, 1H H$_{trans}$-C(8')); 5.22(d, J$_{cis}$ = 8, 1H, H$_{cis}$-C(8')); 3.76(d, J=12, PhCH$_2$N=), 3.73(s, 3H, CH$_3$O); 3.03(d, J=10, 1H PhCH$_2$N=); 2.95-2.85(m, 2H), 2.75-2.65(m, 1H), 2.45-2.35(m, 1H, H—C(6)); 2.2-2.1(m, 1H); 2.05-1.50(m, 7H); 1.4-1.35(m, 1H)<br>Elemental analysis calculated for C$_{16}$H$_{22}$N$_2$<br>calc:   C 79.29   H 9.15   N 11.56<br>found: C 78.61   H 9.42   N 11.22 |
| 11 | 3-methoxyphenyl | 5-(3'-Trimethylbenzyl)-1,5-diazabicyclo[4.3.0]nonane<br>Colourless oil<br>$^1$H NMR($d_6$-DMSO): 7.22(t, 1ArH C(5')); 6.86(s, 1ArH C(2')); 6.81 and 6.74(each d, 2ArH C(4') and C(6')); 3.76 (d, J=12, PhCH$_2$N=), 3.73(s, 3H, CH$_3$O); 3.0(d, J=10, 1H PhCH$_2$N=); 2.95-2.85(m, 2H), 2.75-2.65(m, 1H), 2.45-2.35(m, 1H, H—C(6)); 2.2-2.1(m, 1H); 2.05-1.45(m, 7H); 1.4-1.3(m, 1H)<br>Elemental analysis calculated for C$_{15}$H$_{22}$N$_2$O<br>calc.:  C 73.13   H 9.00   N 11.37<br>found: C 72.96   H 9.09   N 10.71 |
| 12 | 2,3-dichlorophenyl | 5-(2',3'-Dichlorobenzyl)-1,5-diazabicyclo[4.3.0]nonane<br>Colourless crystals, m.p. 123° C.<br>$^1$H NMR($d_6$-DMSO): 7.27(d, J=10, 2ArH C(3' and C5')); 7.12(t, J=10, 1ArH C(4')); 3.98(d, J=15, 1H PhCH$_2$N=), 3.59(d, J=15, 1H PhCH$_2$N=); 3.15-3.05(m, 2H), 2.8-2.7(m, 1H, H—C(6)), 2.55-2.5(m, 1H), 2.3-2.2(m, 1H); 2.2-1.65(m, 7H)1.5-1.4(m, 1H)<br>Elemental analysis for C$_{14}$H$_{18}$Cl$_2$N$_2$:<br>calc.:  C 58.96   H 6.36   N 9.82<br>found: C 59.28   H 6.62   N 9.84 |

TABLE 2-continued

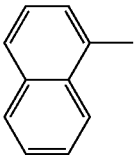

| Example | Ar | Name and analytical data<br>1H NMR[ppm]/Elemental analysis[%] |
|---------|----|----|
| 13 | (naphth-1-yl) | 5-(Naphth-2-yl-methyl-1,5-diazabicyclo[4.3.0]nonane<br>Yellowish crystals, m.p. 72° C.<br>$^1$H NMR(CDCl$_3$): 8.45(d, 1ArH); 7.83(d, 1ArH); 7.76(d, 1ArH); 7.55-7.45(m, 3ArH); 7.38(m, 3ArH); 4.43(d, J=15, PhCH$_2$N=); 3.41(d, J=10, 1H PhCH$_2$N=); 3.2-3.05 (m, 2H), 2.75-2.65(m, 1H), 2.50-2.45(m, 1H, H—C(6)); 2.3-2.2(m, 1H); 2.2-1.7(m, 7H); 1.4-1.35(m, 1H)<br>Elemental analysis for C$_{18}$H$_{22}$N$_2$:<br>calc.: C 81.16  H 8.32  N 10.52<br>found: C 80.98  H 8.48  N 10.34 |

EXAMPLE 14

Preparation of 1,4-bis(1,5-diazabicyclo[4.3.0]nonanylmethyl)benzene

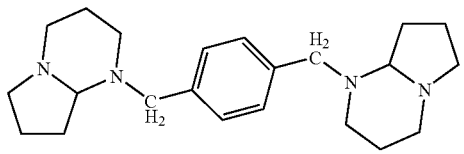

This compound is prepared by the method described for Example 7 using 0.5 mol equivalents of 1,4-dichloromethyl-benzene as the aralkyl halide. The product is obtained as a colourless solid having a m.p. of 110° C.

$^1$H NMR (CDCl$_3$) [ppm]: 7.27 (signals of an AB system, 4 ArH), 3.9 (2H, d, J=1 Hz, PhCH$_2$N=), 3.15-3.05 (m, 4H); 3.04 (2H, d, J=10 Hz, PhCH$_2$N=), 2.90–2.85 (m, 2H) 2.4-2.35 (m, 2H, H—C(6) and H—C(6")); 2.3-2.2 (m, 2H), 2.15-1.6 (m, 14H); 1.5-1.45 (m, 2H).

EXAMPLE 15-17

Preparation of 1,8-diazabicyclo[5.4.0]undecan-8-yl derivatives

The compounds set out in Table 3 are prepared by the method described for Example 7 using 1,8-diaza[5.4.0]undec-7-ene as the amine instead of 1,5-diaza[4.3.0]non-5-ene and using the aralkyl chlorides Ar—CH$_2$—Cl set out in the table.

TABLE 3

| Example | Ar | Name and analytical data<br>1H NMR[ppm]/Elemental analysis [%] |
|---------|----|----|
| 15 | (phenyl) | 8-Benzyl-1,8-diazabicyclo[5.4.0]undecane<br>Colourless oil<br>$^1$H NMR(d$_6$-DMSO): 7.3-7.15(m, 5ArH); 3.83(d, J=15, 1H PhCH$_2$N=), 3.3(d, J=15, 1H PhCH$_2$N=); 3.3-3.25(m, 1H), 3.0-2.9(m, 1H), 2.75-2.65(m, 1H, H—C(7)), 2.65-2.40 (m, 2H); 2.23(m, 1H); 1.95-1.85(m, 1H); 1.75-1.4(m, 8H) 1.35-1.25(m, 1H); 1.15-1.05(m, 1H)<br>Elemental analysis for C$_{16}$H$_{24}$N$_2$:<br>calc.: C 78.64  H 9.90  N 11.46<br>found: C 78.16  H 10.22  N 11.29 |

TABLE 3-continued

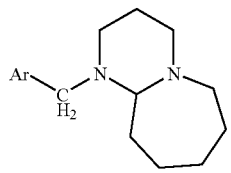

| Example | Ar | Name and analytical data 1H NMR[ppm]/Elemental analysis [%] |
|---|---|---|
| 16 | ![2-chlorophenyl] | 8-(2'-Chlorobenzyl)-1,8-diazabicyclo[5.4.0]undecane<br>Colourless oil<br>$^1$H NMR($d_6$-DMSO): 7.55-7.45(m, 1ArH); 7.4-7.35(m, 1ArH); 7.35-7.15(m, 2ArH); 3.9(d, J=15, 1H PhCH$_2$N═); 3.65-3.55(m, 1H); 3.47(d, J=15, 1H PhCH$_2$N═); 3.45-3.35(m, 1H), 2.95-2.85(m, 2H), 2.7-2.65(m, 1H, H—C(7)), 2.6-2.40(m, 2H); 2.23(m, 1H); 1.95-1.4(m, 8H) 1.3-1.25 (m, 1H); 1.15-1.05(m, 1H)<br>Elemental analysis for C$_{16}$H$_{23}$ClN$_2$:<br>calc.:  C 68.92    H 8.31    N 10.05<br>found: C 68.56    H 8.61    N 9.65 |
| 17 | ![2,6-dichlorophenyl] | 8-(2',6'-Dichlorobenzyl)-1,8-diazabicyclo[5.4.0]undecane<br>Beige solid, m.p. 86° C.<br>$^1$H NMR(CDCl$_3$): 7.26(d, J=7.5, 2ArH, H—C(3') and H—C(5')); 7.14(t, J=7.5, 1ArH, H—C(4')); 4.13(d, J=15, 1H PhCH$_2$N═), 3.77(d, J=15, 1H PhCH$_2$N═); 3.45-3.35(m, 1H); 3.05-2.95(m, 1H); 2.95-2.85(m, 1H, H—C(7)), 2.75-2.65(m, 2H); 2.6-2.40(m, 2H); 2.15-2.05(m, 1H); 2.0-1.85(m, 2H); 1.8-1.65(m, 2H); 1.65-1.45(m, 3H)1.4-1.25 (m, 2H)<br>Elemental analysis for C$_{16}$H$_{22}$Cl$_2$N$_2$:<br>calc.:  C 61.35    H 7.08    N 8.94<br>found: C 61.52    H 7.19    N 8.85 |

EXAMPLE 18

Preparation of 4-(diazabicyclo[4.3.0]nonanylmethyl)-1,1'-biphenyl

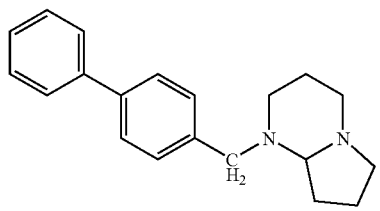

This compound is prepared by the method described for Example 7, using 1.0 mol equivalent of 4-(chloromethyl)-1,1'-biphenyl as the alkyl halide. The compound is obtained as a yellowish oil.

Elemental analysis calculated for C$_{20}$H$_{24}$N$_2$:

| calc.: | C 82.15 | H 8.27 | N 9.58 |
|---|---|---|---|
| Found: | C 82.20 | H 8.48 | N 9.22 |

$^1$H NMR (CDCl$_3$) [ppm]: 7.60-7.25 (9H, m, ArH), 3.95 (d, J=15 Hz, 1H ArCH$_2$N═), 3.10 (1H, d, J=15 Hz, ArCH$_2$N═), 3.15-3.05 (m, 2H), 2.90-2.85 (m, 1H, H—C(6)), 2.45-2.40 (m, 1H), 2.24 (q, J=7.5, 1H); 2.15-1.95 (m, 2H), 1.95-1.55 (m, 5H); 1.47 (D with FS, J=7.5; 1H).

EXAMPLE 19

Preparation of 4,4'-bis(diazabicyclo[4.3.0]nonanylmethyl)-11'-biphenyl

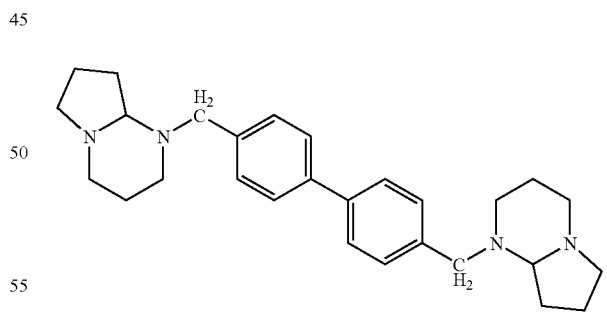

This compound is prepared by the method described for Example 7, using 0.5 mol equivalent of 4,4'-bis(chloromethyl)-1,1'-biphenyl as the alkyl halide. The crude product is obtained as a yellow oil and is purified by chromatography on silica gel (eluent: 3:1 acetone/methanol).

$^1$H NMR (CDCl$_3$) [ppm]: 7.55-7.15 (8H, m, ArH), 3.96 (d, J=15 Hz, 2H ArCH$_2$N═), 3.10 (2H, d, J=15 Hz, ArCH$_2$N═), 3.15-3.05 (m, 4H), 2.90-2.85 (m, 2H), 2.45-2.40 (m, 2H), 2.25 (q, J=7.5, 2H); 2.20-2.00 (m, 4H), 2.00-1.55 (m, 10H); 1.48 (D with FS, J=7.5; 2H).

EXAMPLE 20

Preparation of 5-benzyl-2-methyl-1,5-diazabicyclo[4.3.0]nonane

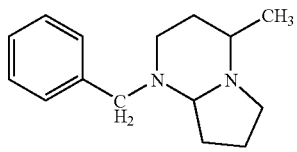

20.1: 3-[1,3]-Dioxolan-2-yl-propionitrile 58.8 g (1.2 mol) of sodium cyanide and 22.28 g (0.12 mol) of benzyltrimethylammonium chloride are dissolved in 360 ml of water. Thereafter 181.03 g (1.0 mol) of 2-[1,3]-dioxolan-2-yl-1-bromoethane are added dropwise and the reaction mixture is heated at 90° C. After six hours it is cooled, diluted with 400 ml of water and subjected to extraction with ether. Drying over magnesium sulfate and evaporation of the solvent give 111.85 g of 3-[1,3]-dioxolan-2-yl-propionitrile as a reddish oil which is used without further purification in the next stage of the reaction.

$^1$H NMR (CDCl$_3$) [ppm]: 5.03 (t, J=7.5 Hz, 1H); 4.05-3.85 (m, 4H, H on dioxolane ring), 2.47 (t, J=7.5, 2H—C(2)); 2.1-2.0 (m, 2H—C(3)). IR (film): 2230 cm$^{-1}$ (nitrile).

20.2: 3-[1,3]-Dioxolan-2-yl-propylamine 50.1 g (1.32 mol) of lithium aluminium hydride are suspended in 500 ml of ether. Added dropwise to this suspension is a solution of 111.9 g (0.88 mol) of 3-[1,3]-dioxolan-2-yl-propionitrile.

The mixture is subsequently heated at reflux for 2.5 hours. After cooling, 50 g of water, 50 g of 10% strength sodium hydroxide solution and a further 150 g of water are added. The mixture is then filtered and the filtrate is dried over calcium chloride and concentrated.

The orange oil obtained is subsequently distilled under reduced pressure (overhead temperature=46° C., p=0.016 mbar). This gives 68.4 g of 3-[1,3]-dioxolan-2-yl-propylamine.

$^1$H NMR (CDCl$_3$) [ppm]: 4.88 (t, J=7.5 Hz, 1H); 4.00-3.80 (m, 4H, H on dioxolane ring), 2.73 (t, J=7.5, 2H—C(2)); 1.75-1.65 (m, 2H); 1.65-1.50; 1.15 (broad s, 2HN).

20.3: 3-(3-[1,3]-Dioxolan-2-yl-propylamino)butyronitrile 49.85 g (0.38 mol) of 3-[1,3]-dioxolan-2-yl-propylamine and 43.34 g (0.646 mol) of crotononitrile are combined in a 200 ml round-bottomed flask and heated at 100° C. for 72 hours. After cooling, the brown mass is diluted with ethyl acetate and washed with water. The organic phase is dried over calcium carbonate and purified by filtration on silica gel (eluent: ethyl acetate). Evaporation of the solvent gives 69.8 g of 3-(3-[1,3]-dioxolan-2-ylpropylamino)butyronitrile as a reddish liquid which is used without further purification in the next stage.

$^1$H NMR (CDCl$_3$) [ppm]: 4.88 (t, J=7.5 Hz, 1H); 4.05-3.80 (m, 4H, H on dioxolane ring), 3.02 (sextet, 1H, H—C(3)); 2.65 (t, J=7.5, 2H HC(6); 5H), 2.44 (d, J=7.5; 2H); 1.75-1.5 (m, 4H); 1.25 (d, J=7.5, 3H CH$_3$—C(3)); 1.2 (broad s, 1H NH). IR (film): 2240 cm$^{-1}$ (nitrile).

20.4: 3-(3-([1,3]-Dioxolan-2-yl)propylamino)-1-aminobutane

In a 1.5 liter sulfonating flask, 10.7 g (0.282 mol) of lithium aluminium hydride are suspended in 620 ml of diethyl ether. Then 55.9 g (0.282 mol) of 3-(3-[1,3]dioxolan-2-yl-propylamino)butyronitrile in solution in 210 ml of diethyl ether are slowly added dropwise. The mixture is subsequently heated at 35° C. for three hours. After cooling to 0° C., 10.7 g of water, 10.7 g of 10% strength NaOH and then a further 32.1 g of water are carefully added dropwise. The reaction solution is filtered over Hyflo and concentrated under reduced pressure. This gives 49.86 g of 3-{3-([1,3]dioxolan-2-yl)propylamino}-1-aminobutane as a reddish liquid which is used without further purification in the next stage.

$^1$H NMR (CDCl$_3$) [ppm]: 4.88 (t, J=7.5 Hz, 1H); 4.05-3.85 (m, 4H, H on dioxolane ring), 2.85-2.55 (m, 5H), 1.75-1.4 (m, 6H); 1.45 (broad s, 3H; 2 HN(1), 1 HN (3)); 1.7 (d, J=7.5, 3H CH$_3$—C(3)).

20.5: 2-Methyl-1,5-diazabicyclo[4.3.0]nonane

In a 500 ml three-necked flask, 41.08 g (0.2 mol) of 3-(3-([1,3]dioxolan-2-yl) propylamino)-1-aminobutane are added to 65 g of 33% strength hydrochloric acid and 100 ml of water and the mixture is stirred vigorously for three hours. It is then neutralized by dropwise addition of 100 ml of 30% strength sodium hydroxide solution, and the neutralized solution is subjected to extraction with CH$_2$Cl$_2$. The organic extracts are dried over sodium carbonate and concentrated. This gives 27.54 g of a reddish liquid. Distillation under a high vacuum (overhead temperature=34° C., p=0.006 mbar) gives 15.87 g of 1,5-diazabicyclo[4.3.0]nonane as a colourless oil.

$^1$H NMR (CDCl$_3$) [ppm]: 3.23 (txd, J=7.5/3 Hz, 1H); 3.12 (dxd, J=10/5 Hz, 1H), 2.88 (dxd, J=7.5/5 Hz 1H), 2.73 (txd, J=7.5/3 Hz, 1H); 2.30-2.20 (m, 1H); 2.10-1.95 (m, 2H), 1.70 (m, 1H): 1.65 (m, 1H); 1.55-1.40 (m, 2H); 1.35-1.20 (m, 2H); 1.12 (d, J=7.5, 3H CH$_3$—C(2)).

20.6: 5-Benzyl-2-methyl-1,5-diazabicyclo[4.3.0]nonane

A 250 ml sulfonating flask is charged with 2.53 g of benzyl chloride in 40 ml of toluene, and 2.76 g (0.02 mol) of potassium carbonate are added. The resulting suspension is admixed with 0.33 g (0.002 mol) of potassium iodide and then 2.8 g (0.02 mol) of 2-methyl-1,5-diazabicyclo[4.3.0]nonane, in solution in 10 ml of toluene are slowly added dropwise with stirring. The suspension is thereafter stirred at room temperature for 20 hours and then heated at reflux for two hours. After cooling, the reaction solution is poured into water and the aqueous phase is subjected to repeated extraction with toluene. The combined organic phases are dried over potassium carbonate and concentrated. This gives an orange-red oil which according to $^1$H NMR contains, in addition to several impurities, 5-benzyl-2-methyl-1,5-diazabicyclo[4.3.0] nonane as the main product.

For further purification, this oil is chromatographed on silica gel using 3:1 acetone/methanol as eluent. The collected fractions containing pure product, following concentration, give 2.36 g of pure 5-benzyl-2-methyl-1,5-diazabicyclo [4.3.0]nonane as a pale yellowish oil.

$^1$H NMR (CDCl$_3$) [ppm]: 7.35-7.15 (5H, m, ArH), 3.94 (d, J=15 Hz, 1H PhCH$_2$N=), 3.28 (m, 1H); 3.04 (d, J=15 Hz, 1H, PhCH$_2$N=), 2.85-2.75 (m, 1H, H—C(6)), 2.50-2.4 (m, 1H); 2.20-2.00 (m, 3H); 1.95-1.45 (m, 6H), 1.12 (d, J=7.5 3H, CH$_3$—C(2)).

The structure is confirmed by a mass spectrum (MH+=231).

EXAMPLE 21

Curing of a Two-Component Clearcoat 21.1: Preparation of a urethane acrylate based on isophorone diisocyanate and 4-hydroxy-butyl acrylate.

The reaction is carried out under a nitrogen atmosphere, with all of the commercial chemicals used being employed without further purification. 1566.8 g (13.78 mol of NCO) of isophorone diisocyanate, 2.3 g of dibutyltin dilaurate, 2.3 g of 2,5-di-t-butyl-p-cresol and 802.8 g of butyl acetate are charged to a three-necked flask with condenser and apparatus for dropwise addition. Dry nitrogen is sparged through the reaction mixture and the temperature is slowly increased to 60° C. 1987 g (13.78 mol) of 4-hydroxy-butyl acrylate are added, and the reaction solution slowly warms to 80° C. The temperature is held at 80° C. and the dropwise addition apparatus is rinsed with butyl acetate (86.6 g). By titration for the remaining amount of isocyanate, the reaction is monitored, and is ended when the isocyanate content is less than 0.2%, based on solids. A reaction product having the following physical properties is obtained:

Remaining amount of 4-hydroxybutyl acrylate: <0.002% based on solids (HPLC analysis),
Colour: <<Gardner 1,
Viscosity: 43 cPa s (20° C.),
Solids: 79.3% (1 hour at 140° C.),
GPC data (polystyrene standard) $M_n$ 778, $M_w$ 796, d=1.02.

21.2: Preparation of a Malonate Polyester

The reaction is carried out under a nitrogen atmosphere, with all of the commercial chemicals used being employed without further purification.

In a reaction vessel with stirrer and condenser, 1045 g of 1,5 pentanediol, 1377.4 g of diethyl malonate and 242.1 g of xylene are carefully heated at reflux. The maximum temperature of the reaction mixture is 196° C., while the temperature at the top of the condenser is held at 79° C. In this way 862 g of ethanol are distilled off, corresponding to a conversion of 97.7%. Xylene is then stripped off under reduced pressure at a temperature of 200° C. The polymer obtained has a solid of 98.6%, a viscosity of 2710 mPa s and an acid number of 0.3 mg KOH/g based on solids. $M_n$ is 1838, $M_w$ is 3186, and the colour is 175 on the APHA scale American Public Health Association; "Hazen" colour number; ISO 6271).

21.3: Preparation of the Photopolymerizable Formulation

The two resin components prepared as described in 21.1 and 21.2 are mixed in a weight ratio of 1:2.125. Then 0.5 part of Byk 306 (Byk Chemie) (10% in butyl acetate) is added. Also added to the formulation are 0.5% of sensitizer, benzophenone, "BP" (Fluka) or a mixture of 2-isopropylthioxanthone and 4-isopropylthioxanthone, "ITX" ($^{RTM}$QUANTACURE ITX, Rahn AG) and 2.5% of the initiators set out in Table 4.

Reactivity testing takes place on a dry time measuring apparatus (Byk-Rekorder from Byk Gardner). A needle is drawn at constant rate over a planar glass plate. The photoinitiator-comprising formulation is applied to this glass plate using a doctor blade with a slot height of 75 μm. During the measurement, the measuring apparatus is exposed to light using two daylight lamps (Original Hanau 40 W 001660) at a distance of 1 m. Stage 1 reflects the time at which the components have not yet reacted with one another. Subsequently, gelling and curing of the formulation begin. At the time indicated by Stage 3 in the results in Table 4, the curing of the formulation is at an end. The shorter the time taken to reach the individual stages, the more reactive the formulation. The measured times are listed in Table 4 in the columns headed "1" and "Stage 3".

In order to test the hardness and the yellowing, the formulations are applied to white-primed chipboard panels using a doctor blade with a slot height of 100 μm. Curing takes place under 6 TL 40 W/03 (Phillips) lamps for a period of 24 hours. This is followed by measurements of the König pendulum hardness (DIN 53157) and the CILAB yellow value b* (DIN 6174). The pendulum hardnesses measured are listed in Table 4 in the "PH" column, the yellow values in the column headed "b*".

TABLE 4

| Compound from example | Sensitizer | Stage 1 [h] | Stage 3 [h] | PH [sec] | b* |
|---|---|---|---|---|---|
| 1 | BP | 2 | 4.5 | 49 | 3.9 |
| 2 | BP | 1 | 3.25 | 15 | 10.7 |
| 11 | BP | 2 | 5 | 27 | 3.9 |
| 13 | BP | 3 | 6.5 | 35 | 4.6 |
| 17 | BP | 3 | 6 | 32 | 4.2 |
| 4 | ITX | 0.25 | 0.5 | 57 | 7.4 |
| 5 | ITX | 0.5 | 0.75 | 45 | 6.9 |
| 7 | ITX | 0.5 | 0.75 | 48 | 67 |
| 9 | ITX | 0.25 | 0.5 | 43 | 7.1 |
| 10 | ITX | 1.75 | 2 | 50 | 6.4 |
| 14 | ITX | 0.5 | 0.75 | 48 | 7.4 |

BP = benzophenone;
ITX = isopropylthioxanthone

EXAMPLE 22

Determination of the storage stability of the two-component clearcoat The storage stability of the two-component clearcoat is described in Example 21 with 2.5% of the photolatent amine from Example 1 and 0.5% of benzophenone is determined. For this purpose the sample is stored in the dark at room temperature for a period of 2 months. The parameter measured is the viscosity in Poise. If the viscosity does not rise significantly within the observation period, the formulation is considered to be stable on storage. Over the period of observation, the sample measured is stable on storage.

What is claimed is:
1. A compound to of the formula

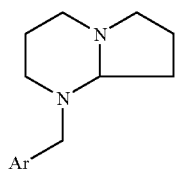

wherein Ar
is capable of absorbing light in the wavelength range from 200 nm to 650 nm, which on absorption brings about a photoelimination which leads to the generation of an amidine group and is unsubstituted phenyl, naphthyl, phenanthryl, anthryl, thienyl, thianthrenyl, anthraquinonyl, xanthenyl, thioxanthyl, phenoxathiinyl, carbazolyl, fluorenyl or phenoxazinyl;

or phenyl, naphthyl, phenanthryl, anthryl, thienyl, thianthrenyl, anthraquinonyl, xanthenyl, thioxanthyl, phenoxathiinyl, carbazolyl, fluorenyl or phenoxazinyl substituted one or more times by $C_1$-$C_{18}$alkyl, $C_2$-$C_{18}$alkenyl, $C_1$-$C_{18}$haloalkyl, $NO_2$, $NR_{10}R_{11}$, CN, $OR_{12}$, $SR_{12}$, $C(O)R_{13}$, $C(O)OR_{14}$, halogen or a radical of the formula II

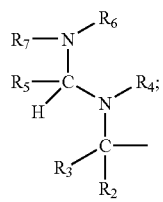

(II)

wherein
 $R_2$ and $R_3$ are hydrogen,
 $R_4$ and $R_6$ together form a propylene bridge;
 $R_5$ and $R_7$ together form a propylene bridge or a pentylene bridge;
 $R_{10}$, and $R_{11}$ independently of one another are hydrogen or $C_1$-$C_{18}$alkyl;
 $R_{12}$, $R_{13}$ and $R_{14}$ independently of one another are hydrogen or $C_1$-$C_{18}$alkyl;
 or Ar is a radical of the formula III

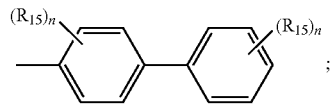

(III)

wherein $R_{15}$ is $C_1$-$C_{18}$alkyl, OH, CN, $OR_{10}$, halogen or a radical of formula II; and n is 0 or 1.

2. A compound to of the formula

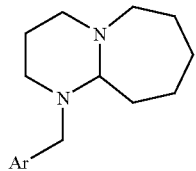

wherein Ar is capable of absorbing light in the wavelength range from 200 nm to 650 nm, which on absorption brings about a photoelimination which leads to the generation of an amidine group and is unsubstituted phenyl, naphthyl, phenanthryl, anthryl, thienyl, thianthrenyl, anthraquinonyl, xanthenyl, thioxanthyl, phenoxathiinyl, carbazolyl, fluorenyl or phenoxazinyl;

or phenyl, naphthyl, phenanthryl, anthryl, thienyl, thianthrenyl, anthraquinonyl, xanthenyl, thioxanthyl, phenoxathiinyl, carbazolyl, fluorenyl or phenoxazinyl substituted one or more times by $C_1$-$C_{18}$alkyl, $C_2$-$C_{18}$alkenyl, $C_1$-$C_{18}$haloalkyl, $NO_2$, $NR_{10}R_{11}$, CN, $OR_{12}$, $SR_{12}$, $C(O)R_{13}$, $C(O)OR_{14}$, halogen or a radical of the formula II

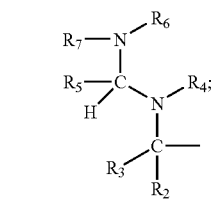

(II)

wherein
 $R_2$ and $R_3$ are hydrogen,
 $R_4$ and $R_6$ together form a propylene bridge;
 $R_5$ and $R_7$ together form a propylene bridge or a pentylene bridge;
 $R_{10}$, and $R_{11}$ independently of one another are hydrogen or $C_1$-$C_{18}$alkyl;
 $R_{12}$, $R_{13}$ and $R_{14}$ independently of one another are hydrogen or $C_1$-$C_{18}$alkyl;
 or Ar is a radical of the formula III

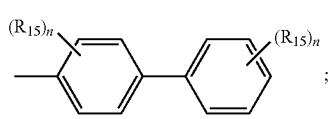

(III)

wherein $R_{15}$ is $C_1$-$C_{18}$alkyl, OH, CN, $OR_{10}$, halogen or a radical of formula II; and n is 0 or 1;
with the proviso that 8-benzyl-1,8-diazabicyclo[5.4.0]undecane is excluded.

\* \* \* \* \*